US012642673B2

(12) United States Patent
Wills et al.

(10) Patent No.: US 12,642,673 B2
(45) Date of Patent: Jun. 2, 2026

(54) DEVICE FOR ASSEMBLING IMPLANT SYSTEMS

(71) Applicant: Encore Medical, L.P., Austin, TX (US)

(72) Inventors: Kevin Michael Wills, Austin, TX (US); David Link, Austin, TX (US); Heather Fewell, Spring, TX (US); Adam Shallenberg, Austin, TX (US); Annika Westerberg, Austin, TX (US); Michael Nyland, Austin, TX (US); Michael Trolinger, Austin, TX (US)

(73) Assignee: Encore Medical, L.P., Austin, TX (US)

( * ) Notice: Subject to any disclaimer, the term of this patent is extended or adjusted under 35 U.S.C. 154(b) by 526 days.

(21) Appl. No.: 18/053,527

(22) Filed: Nov. 8, 2022

(65) Prior Publication Data

US 2023/0143676 A1     May 11, 2023

Related U.S. Application Data

(60) Provisional application No. 63/263,921, filed on Nov. 11, 2021.

(51) Int. Cl.
*A61F 2/76*     (2006.01)
*A61F 2/36*     (2006.01)
*A61F 2/46*     (2006.01)

(52) U.S. Cl.
CPC .................. *A61F 2/76* (2013.01); *A61F 2/36* (2013.01); *A61F 2/4607* (2013.01); *A61F 2/4637* (2013.01)

(58) Field of Classification Search
CPC . A61F 2/76; B25B 13/22; B25B 5/068; F16H 63/3433; Y10T 74/1529; Y10T 74/1565; Y10T 74/1576; Y10T 74/1582; Y10T 74/1595; F16M 11/041
USPC ..................................................... 296/6; 81/61
See application file for complete search history.

(56) References Cited

U.S. PATENT DOCUMENTS

| | | | |
|---|---|---|---|
| 318,221 A | 5/1885 | Thompson et al. | |
| 464,316 A | 12/1891 | Greenerd | |
| 632,387 A | 9/1899 | White | |
| 754,962 A | * 3/1904 | Bennett .................. | B25B 5/102 |
| | | | 269/146 |
| 947,619 A | * 1/1910 | Orr ......................... | B25B 13/16 |
| | | | 81/161 |
| 1,069,539 A | 8/1913 | Evans, Jr. | |
| 1,103,179 A | 7/1914 | Elliot | |

(Continued)

OTHER PUBLICATIONS

International Search Report and Written Opinion dated Mar. 31, 2023 in application No. PCT/US22/46539.

(Continued)

*Primary Examiner* — David W Bates
(74) *Attorney, Agent, or Firm* — Eversheds Sutherland (US) LLP

(57)     ABSTRACT

An implant assembly device configured to press an inner femoral head into a plastic outer femoral head by means of actuator system. The actuator system embodies a unique pawl system that acts to reduce the occurrence and severity of device jamming due to over compression. The device includes a unique head support apparatus that aligns and orients the inner and outer femoral heads prior to and throughout the assembly process. The device can also include a grip portion integrated onto the body of the device, for holding and stabilizing the device when in use.

20 Claims, 16 Drawing Sheets

(56)          References Cited

U.S. PATENT DOCUMENTS

| | | | | |
|---|---|---|---|---|
| 2,322,471 | A | | 6/1943 | Robertson |
| 2,368,843 | A | | 2/1945 | Kees |
| 2,372,727 | A | * | 4/1945 | Manning ................. B25B 5/101 |
| | | | | 269/189 |
| 2,634,889 | A | * | 4/1953 | Sherbondy .......... B05C 17/0123 |
| | | | | 222/391 |
| 2,845,805 | A | * | 8/1958 | Crewe ................... G01F 11/026 |
| | | | | 222/391 |
| 2,889,085 | A | * | 6/1959 | Collins ................ G01F 11/026 |
| | | | | 222/391 |
| 2,891,302 | A | | 6/1959 | Fuglie et al. |
| 3,357,698 | A | * | 12/1967 | Flynn ..................... B25B 5/101 |
| | | | | 269/221 |
| 3,427,016 | A | * | 2/1969 | Harris .................... B25B 5/068 |
| | | | | 269/215 |
| 3,710,641 | A | * | 1/1973 | Anderson ................ B25B 5/10 |
| | | | | 74/89.37 |
| 4,457,306 | A | | 7/1984 | Borzone |
| 4,676,798 | A | | 6/1987 | Noiles |
| 4,977,660 | A | | 12/1990 | Maynard |
| 5,133,765 | A | | 7/1992 | Cuilleron |
| 5,217,213 | A | * | 6/1993 | Lii .......................... B25B 5/067 |
| | | | | 269/6 |
| 5,823,076 | A | * | 10/1998 | Binkowski ............. B25B 13/22 |
| | | | | 81/127 |
| 5,849,015 | A | | 12/1998 | Haywood et al. |
| 5,857,252 | A | | 1/1999 | Jansen |
| 6,293,971 | B1 | * | 9/2001 | Nelson .................... B29C 43/16 |
| | | | | 623/22.21 |
| 6,296,241 | B1 | | 10/2001 | Harrison |
| 8,313,095 | B2 | * | 11/2012 | Kloepfer ................. B25B 5/163 |
| | | | | 269/166 |
| 2004/0059349 | A1 | * | 3/2004 | Sixto, Jr. ............ A61B 17/0643 |
| | | | | 606/139 |
| 2004/0217531 | A1 | * | 11/2004 | Yates ...................... B25B 1/125 |
| | | | | 269/184 |
| 2007/0162038 | A1 | | 7/2007 | Tuke et al. |
| 2008/0083595 | A1 | | 4/2008 | Speigel et al. |
| 2009/0005784 | A1 | | 1/2009 | Blain et al. |
| 2011/0001283 | A1 | * | 1/2011 | Seber ........................ B25B 1/24 |
| | | | | 269/173 |
| 2012/0186055 | A1 | * | 7/2012 | Chen ................... F16D 65/0043 |
| | | | | 29/239 |
| 2017/0325972 | A1 | | 11/2017 | Steif |
| 2019/0083283 | A1 | | 3/2019 | Sharifi-Mehr et al. |
| 2019/0240028 | A1 | | 8/2019 | Gheevarughese et al. |
| 2020/0222141 | A1 | | 7/2020 | Termanini et al. |

OTHER PUBLICATIONS

Supplementary European Search Report for EP22893550 dated Sep. 22, 2025, 5 pages.

* cited by examiner

FRONT

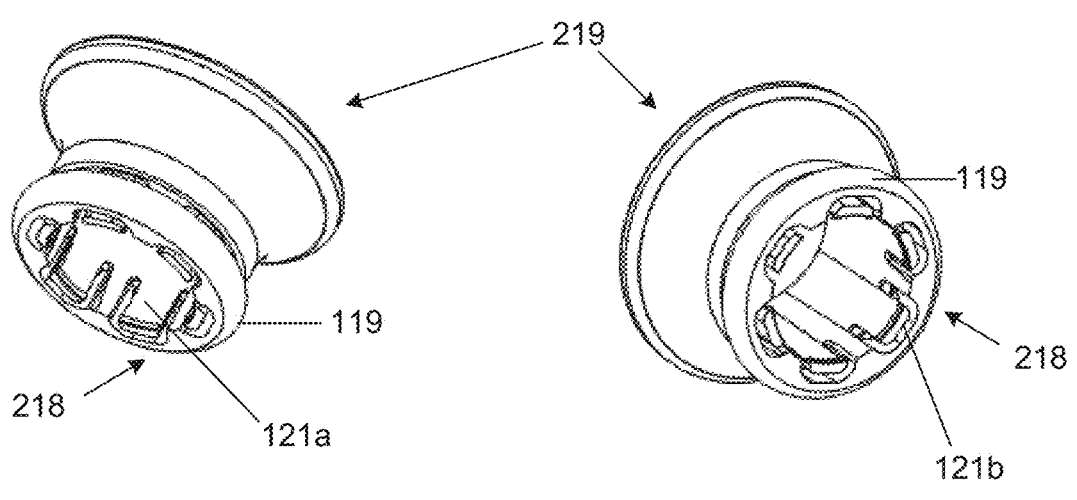
FIG. 8A
FIG. 8B
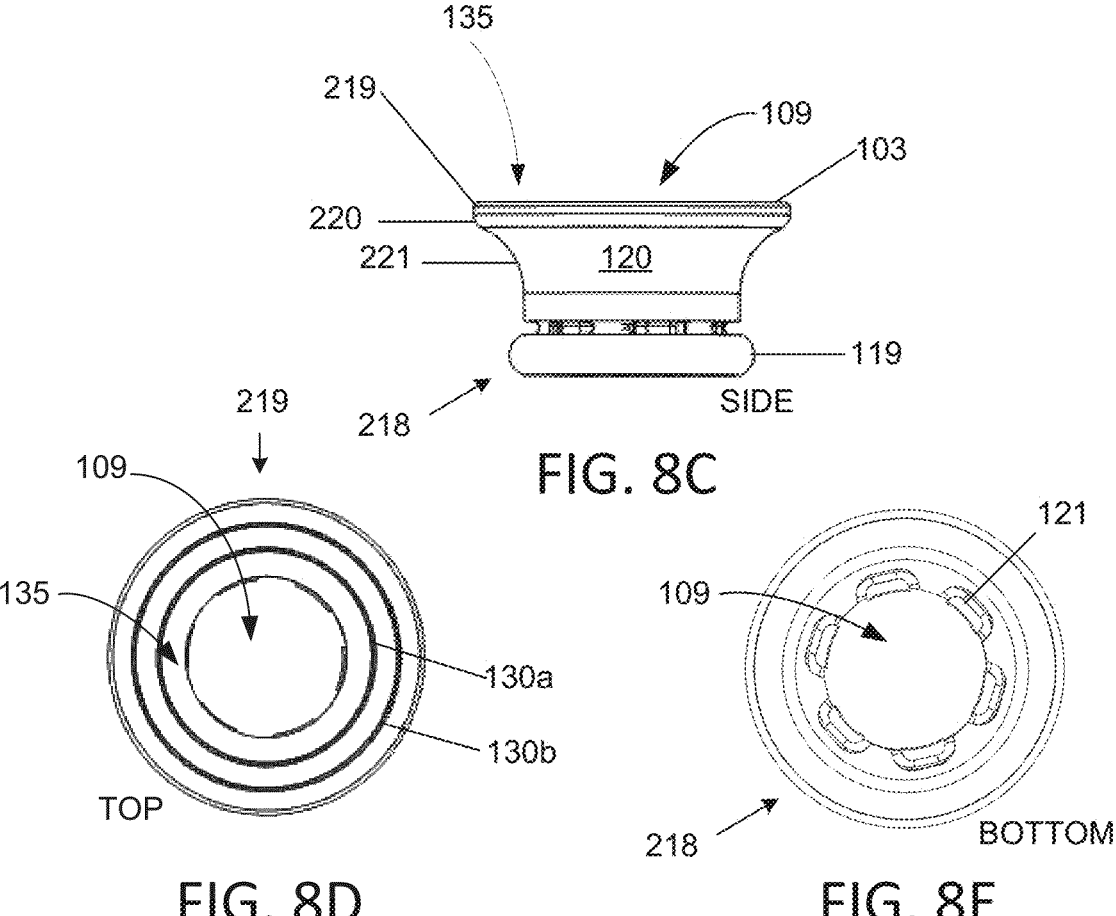
FIG. 8C
FIG. 8D
FIG. 8E

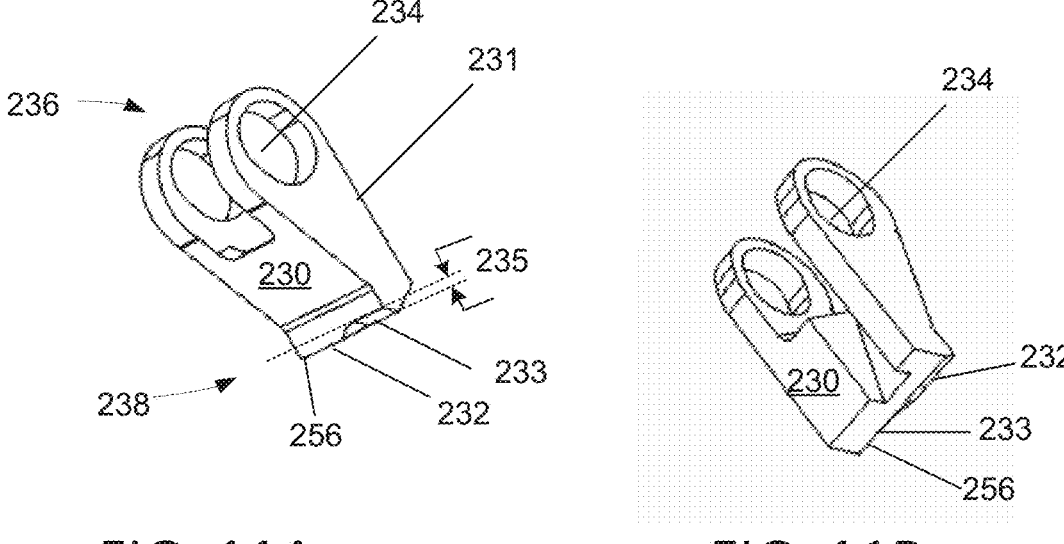
FIG. 11A
FIG. 11B
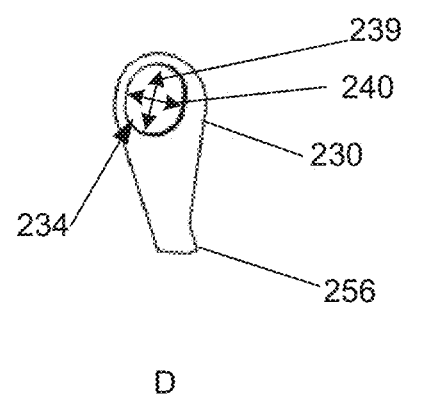
FIG. 11C
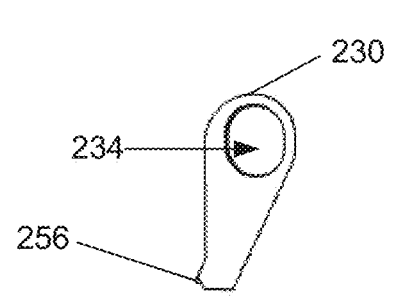
FIG. 11D

TOP

BOTTOM

FRONT

BACK

DEVICE FOR ASSEMBLING IMPLANT SYSTEMS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application claims the benefit of U.S. Provisional Patent Application No. 62/263,921, filed Nov. 11, 2021, the content of which is hereby incorporated by reference herein in its entirety.

BACKGROUND

Field

This disclosure generally relates to assembling multi-component implant systems. More specifically, this disclosure relates to devices and methods for mechanically coupling together two components of an implant system using a hand operated coupling system.

Description of the Related Art

Hip replacement femoral head implants are used in the medical field to replace part or entire hip structures. In some examples, a portion of a femoral implant is designed to be placed into a patient's femur. Femoral head implants may include a ball-like "head" coupled to an upper portion (a "taper") of the femoral implant. The natural socket in the hip joint is replaced with an artificial "cup," an implant that can include a hemispherical-shaped outer shell and a corresponding hemispherical-shaped inner liner nested inside, and coupled to, the outer shell. The inner head and outer head are separate components. Prior to being coupled to the taper portion, the heads are assembled such that the inner head is positioned in the cavity of the outer head. The inner head fits tightly into the outer head, and coupling them together requires a great deal of force. The shape of the outer and inner head can make it difficult to correctly apply the required force quickly without damaging the components. It would be advantageous to have a fast, easy-to-use coupling device to increase efficiency and minimize potential damage to the inner and outer head.

SUMMARY

The devices, systems, and methods of the present disclosure have several features, no single one of which is solely responsible for its desirable attributes. Without limiting the scope of embodiments of the invention as expressed by the claims which follow, certain innovations will now be discussed briefly. After considering this discussion, and other sections provided herein, one will understand how the features of embodiments of the implant system assembly device in this disclosure provide several advantages.

To address problems with assembling the components of a femoral head implant, the disclosure describes aspects of a device for assembling the components of a head efficiently, easily, and without damaging the plastic outer head. One innovation includes a femoral head implant assembly device for coupling together an inner head and an outer head portion, the assembly device comprising a handle, a rod coupled to the handle, the rod aligned along a longitudinal axis and coupled to the handle, a body comprising a distal end and a proximal end, the body having a base portion, a top portion, and a support portion between the base portion and the top portion, the support portion including a grip for a user to hold while moving the handle.

The assembly device can further include an actuator system in the top portion, the actuator system coupled to the rod to move the rod along the longitudinal axis and to allow the rod to be at least partially rotated around the longitudinal axis. The actuator system includes a drive pawl coupled to the handle and configured to engage the rod and drive the rod along the longitudinal axis towards the base portion when the handle is moved from a first position to a second position, and a set pawl configured to engage the rod and hold the rod in place while the handle is moved from the second position to the first position. The assembly system can further include a head support having an inner member coupled to the base portion and positioned between the rod and the base portion, an inner head support extending from the inner member towards the rod and configured to receive an inner head thereon, the inner head support aligned along the longitudinal axis with the rod, and a stage circumferentially positioned around and slidably coupled to the inner member such that the stage can move along an exterior surface of the inner member.

Various embodiments of a device for assembling implant systems include various additional features. For example, the assembly device can further include a cupola coupled to the proximal end of the rod such that the cupola is positioned between the rod and the stage. The cupola can include a concave surface that faces the stage, the concave surface configured to fit against the exterior surface of an outer head portion. In some embodiments, the cupola is frustum shaped.

The set pawl includes a proximal end, having an edge that includes a first portion and a second portion, the first portion of the edge extending further than the second portion of the edge. The extension of the first portion and the second portion define a setback region. In some embodiments, the first portion of the edge has a curved transition to the second portion of the edge. The set pawl includes a distal end and a proximal end, wherein the distal end is movably coupled to the actuator system.

The rod can include teeth on a surface of the rod extending along at least part of the length of the rod, wherein the first portion of the edge of the set pawl is positioned to engage with teeth on the surface of the rod when the teeth are positioned adjacent to the first portion. In some examples, the teeth are aligned perpendicular to the length of the rod.

The set pawl is positioned such that the first portion engages with the teeth of the rod and the second portion does not engage with the teeth of the rod when the rod is positioned with the teeth of the rod aligned in parallel with the edge of the set pawl.

The stage can include a platform on the distal end of the stage. The platform can be aligned substantially normal to the longitudinal axis of the rod. The stage also includes an aperture longitudinally positioned in the center of the platform and sized such that the inner member fits into the aperture. The stage can further include one or more fingers positioned on the interior surface of the aperture and extending into the aperture. The fingers are configured to contact the inner member to provide a friction fit between the stage and the inner member. The friction fit between the fingers and the inner member allow the stage to be positionable at different heights on the inner member. In some embodiments, the body comprises one or more cavities making the assembly device lighter weight. In some embodiments, the platform comprises indicia to guide placement of the outer head on the platform. In some embodiments, the indicia is etched into the platform. In some embodiments, the indicia includes at least one ring surrounding the aperture. In some embodiments, the indicia includes two or more concentric rings.

The stage can include a guard positioned at the proximal end of the stage. The guard is positioned so the user does not get their fingers caught between the stage and the base portion of the device as the stage is lowered.

In some embodiments, the assembly device further includes a base support coupled to the base to provide support for the device.

BRIEF DESCRIPTION OF THE DRAWINGS

The features and advantages of the devices and methods described herein will become more fully apparent from the following description and appended claims, taken in conjunction with the accompanying drawings. These drawings depict only several embodiments in accordance with the disclosure and are not to be considered limiting of its scope. In the drawings, similar reference numbers or symbols typically identify similar components, unless context dictates otherwise. In some instances, the drawings may not be drawn to scale.

FIGS. 8A-8E illustrate a stage shown in FIG. 1, in accordance with an illustrative embodiment, where FIG. 8A depicts a perspective view of the stage in one position, FIG. 8B depicts a perspective view of the stage in a second position, FIG. 8C depicts a front view of the stage, FIG. 8D depicts a top view of the stage, and FIG. 8E depicts a bottom view of the stage.

FIG. 10A depicts a side view of the cupola, FIG. 10B depicts a top view of the cupola, and FIG. 10C depicts a bottom view of the cupola.

FIGS. 11A-11D illustrate a set pawl as shown in FIG. 3, in accordance with an illustrative embodiment, where FIG. 11A depicts a perspective view of the set pawl in one position, FIG. 11B depicts a perspective view of the set pawl in a second position, FIG. 11C depicts a left-side view of the set pawl, and FIG. 11D depicts a right-side view of the set pawl.

FIG. 12A depicts a top view of the set pawl, FIG. 12B depicts a bottom view of the set pawl, FIG. 12C depicts a front view of the set pawl, and FIG. 12D depicts and back view of the set pawl.

DETAILED DESCRIPTION OF CERTAIN INVENTIVE ASPECTS

Figure 1:
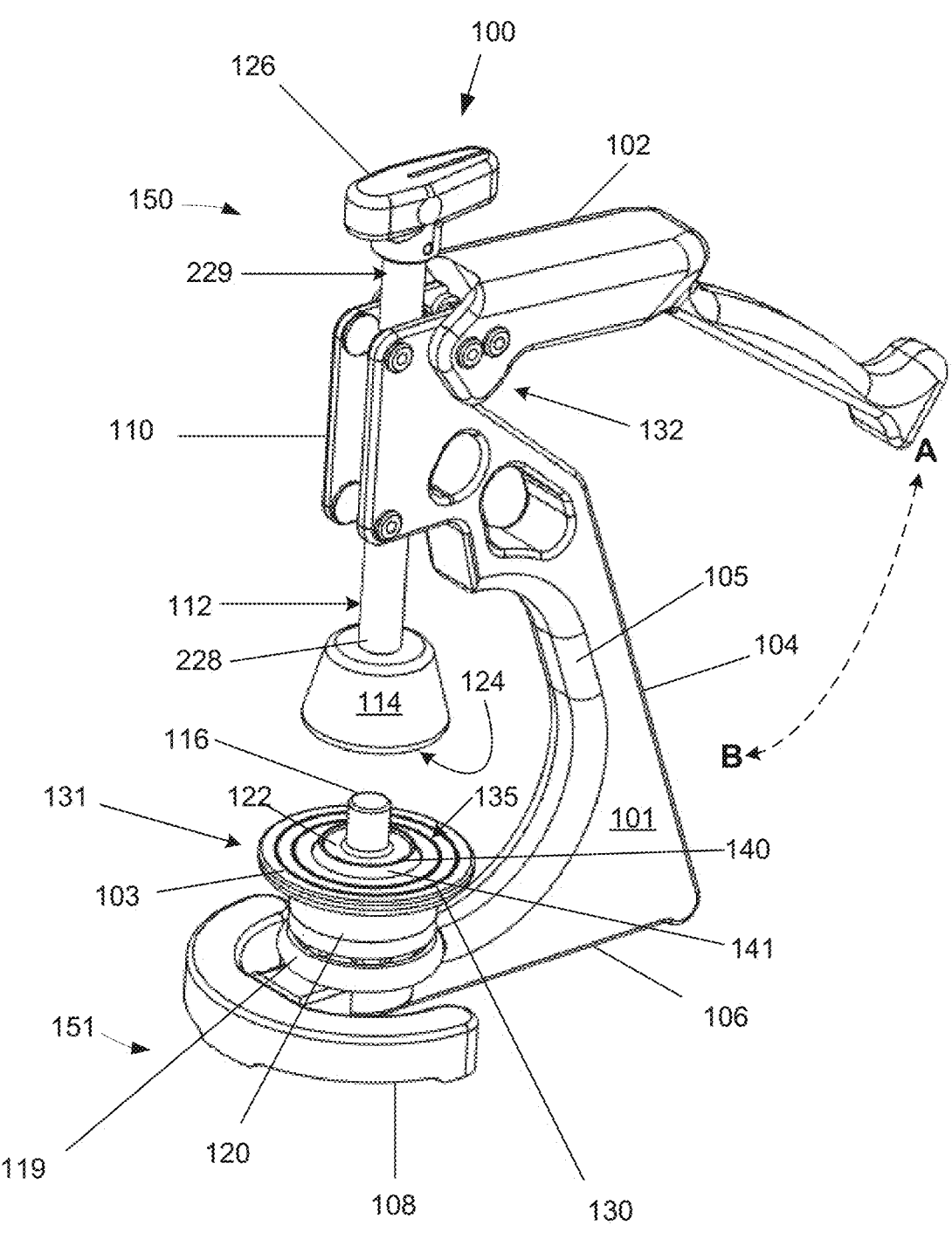
FIG. 1 illustrates a perspective view of a femoral head implant assembly device in accordance with an illustrative embodiment.

The following detailed description is directed to certain specific embodiments of the invention. However, the invention can be embodied in a multitude of different ways. It should be apparent that the aspects herein may be embodied in a wide variety of forms and that any specific structure, function, or both being disclosed herein is merely representative of one or more embodiments of the invention. An aspect disclosed herein may be implemented independently of any other aspects and that two or more of these aspects may be combined in various ways. For example, a device for assembling implant systems includes, or a method of assembling implant systems may be practiced, using any number of the aspects set forth herein. In addition, disclosed devices may be implemented, or such a method may be practiced, using other structure, functionality, or structure and functionality in addition to, or other than one or more of the aspects set forth herein.

Dual mobility hip replacement femoral head implants are used in the medical field to replace part or entire hip structures. In some examples, a portion of a femoral implant is designed to be placed into a patient's femur. A ball-like "head" is coupled to an upper portion (a "taper") of the femoral implant. The natural socket in the hip joint is replaced with an artificial "cup," an implant that can include a hemispherical-shaped outer shell and a corresponding hemispherical-shaped inner liner nested inside, and coupled to, the outer shell. When the inner liner is nested inside the cup, a concave surface of the inner liner faces away from the cup and is designed to receive the head coupled to the femoral implant. The head includes a hard (rigid) inner head component ("inner head") and a plastic larger outer head component ("outer head"). The outer head includes an opening and a cavity shaped and sized to receive the inner head.

In some examples, the outer head can comprise polyethylene, or other suitable materials. In some embodiments, the outer head comprises HXe+™ polyethylene, a highly-cross-linked material designed for ball and socket kinematics, and which are blended with Vitamin E. The inner head and outer head are separate components, but prior to being coupled to the taper portion, the heads are assembled such that the inner head is positioned in the cavity of the outer head. Once assembled, the inner head must be retained within the outer head for proper function and patient safety. The inner head is retained within the outer head by under-sizing the opening of the outer head, or other feature, such that it takes a large amount of force to assemble the inner head through the opening and into the cavity; and therefore, accidental dissociation also requires a large amount of force. Due to the force required to assemble the inner head and the outer head, and because the plastic outer head is susceptible to damage, it can be difficult and time consuming to properly place the inner head in the cavity of the outer head.

Overview of Technology

A damaged or arthritic hip joint can cause pain and decreased mobility and may necessitate hip replacement surgery. Hip replacement surgery involves removal of at least part of a hip joint and replacement with a prosthetic implant. In a total hip replacement surgery, both the femoral head and the acetabulum of the damaged hip joint are replaced. A newer implant known as "dual mobility" provides a greater range of motion and has been shown to reduce the risk of instability in younger, more active patients. A typical hip replacement implant is a ball-in-socket mechanism designed to simulate a human hip joint. Dual mobility implants provide an additional bearing surface compared to a traditional implant. With the dual mobility hip, a large polyethylene plastic head fits inside a polished metal or ceramic hip socket component, and an additional smaller metal or ceramic head is fitted within the polyethylene head.

Dual mobility systems and used an assembly fixture to press the hard (metal or ceramic) inner head into the large polyethylene head. This action happens in the operating room away from the patient. FIGS. 13A-13D illustrate an example of portions of the assembly fixture fitting the inner head 133 into a cavity of the outer head 134. Some systems use a C-clamp style fixture, where the implant components are pressed together by turning a threaded rod, however, such a system can be slow to use due to having to repeatedly turn the threaded rod, or a piece that is coupled to the threaded rod. Embodiments of the subject assembly fixture is such that the handle is squeezed while the fingers grasp the body of the fixture, level with where the implants are located while being pressed together. The unique orientation provides a compact overall envelope, which is needed for instrument transportation and sterility. The orientation of the handle also permits the user to press downward with body weight, while squeezing, providing additional force if needed. This orientation allows for a very stable setup as the fixture is gripped by the user near the center of mass. The assembly fixture includes a unique 'floating platform' feature, which simplifies preparing the implants for being pressed together. In addition, the floating platform provides quick and easily alignment for the implants as they are being pressed together. The platform slides up around the hard inner head and provides a flat/stable surface for the large outer poly head to rest on. Getting the large poly head to be flat and aligned with the hard inner head is a challenge for fixtures that position the poly head above the inner head during pressing. Then, while the poly head is being pressed, the platform is able to slide downward, which maintains the orientation of the poly head.

The assembly fixture also includes two toothed cams or pawls, one drives the movement and applies the force during the press (referred to herein as the "drive pawl"), the other (referred to herein as the "set pawl") prevents the rod from returning upwards while the handle returns upward after a press. That means that when the handle is squeezed, released and squeezed again, the rod will always continue pressing downward. When the user is finished pressing and wants to lift the rod back up, they would spin the rod to disengage the teeth and the rod would be free to move upward. What is unique is the shape of the set pawl, in particular, the edge of the set pawl that engages the teeth on the rod. This design addresses a specific problem condition: when the teeth jam due to the assembly fixture being compressed beyond what is necessary by the user. The jam is caused by that extra compressive force holding the set pawl tooth and rod tooth together. The unique features of the set pawl are twofold. First, the modified tooth allows the set pawl to slip out of this condition without adding additional compressive forces and frees the jam with much less exertion by the user. Without this modified tooth design, rotating the rod (to disengage the teeth and reset the fixture) actually further drives the rod downward, as the pawl rotates and extends in the axis of the rod, which increase the severity of the jam condition. Second, the pawl is not assembled with a true pin-in-hole style assembly, which only allows for a rotational degree of freedom. The pawl can also translate a finite amount in the axis of the rod, to allow the rod to back off the implants it is pressing and reduce the stored stress in the fixture.

The assembly system described herein is advantageous at least because it allows a quicker assembly of the inner and outer head, and thus it is a more efficient way of preparing the implants. The femoral head implant assembly device for assembling implant systems, components of such devices, and methods of using implant assembly systems are disclosed herein. In some embodiments, the femoral head implant assembly system can include a body comprising a base portion and a top portion, and a support coupled to the base and the top portion that includes a grip so that a user can hold the assembly system. The femoral head implant assembly system can also include a rod, a handle, and an actuator system coupled to the rod and the handle, and configured to move the rod when the handle is moved. In some embodiments, the actuator system can include a set pawl that engages with structures (e.g., teeth) on the rod. The set pawl can have a two-part edge, one part being setback to allow the set pawl to release from engagement with the teeth when the rod is rotated around its longitudinal axis. The femoral head implant assembly system can also include a movable or "floating" platform movable along an inner vertical member coupled to the base portion that holds a portion of an implant and move along the vertical member during assembly of the implant. The assembly system can include a cupola coupled to a proximal end of the rod, the cupola used to press on the implant.

The following is a list of certain annotations and components that are described and enumerated in this disclosure in reference to the above-listed figures. However, any aspect, structure, feature or operational function of the devices illustrated in the figures, whether or not named out separately herein, can form a portion of various embodiments and may provide basis for one or more claim limitation relating to such aspects, with or without additional description. The annotations and enumerated components include:

| | |
|---|---|
| 100 femoral head assembly system | 115 outer distal edge of inner member |
| 101 body | 116 inner head support |
| 102 handle | 117 indent |
| 103 platform | 118 set pawl spring |
| 104 support | 119 guard |
| 105 grip | 120 stage |
| 106 base | 121 structures (fingers) |
| 107 body cavities | 122 inner member |
| 108 base support | 123 distal edge of |

-continued

| | |
|---|---|
| 109 aperture | inner head support |
| 110 top portion | 124 lower (proximal) |
| 111 drive pawl | surface of cupola |
| 112 rod | 125 coupling member |
| 113 drive pawl spring | 126 disengagement knob |
| 114 cupola | 128 locking |
| 131 head support | movement assembly |
| 132 actuator system | 129 coupling member head |
| 133 inner head | 130a-b target rings (indicia) |
| 134 outer head | 226 distal end of |
| 135 top or top (distal) surface | inner member |
| 136 surface of rod | 227 teeth of rod |
| 137 first position | 228 proximal end of rod |
| 138 second position | 229 distal end of rod |
| 139 third position | 230 set pawl |
| 140 (peripheral ) ridge | 231 body of set pawl |
| on inner member | 232 first portion of set pawl |
| 141 beveled surface | 233 second portion (setback |
| 150 distal end of | region) of set pawl |
| assembly system | 234 holes of set pawl |
| 151 proximal end of | 235 setback region |
| assembly system | 236 distal end of set pawl |
| 202 longitudinal axis | 238 proximal end of set pawl |
| 218 proximal end of stage | 239 length of hole |
| 219 distal end of stage | of set pawl |
| 220 exterior surface | 240 width of |
| (on side of stage) | hole of set pawl |
| 221 side of stage | 252 distal end of cupola |
| 222 proximal end | 254 proximal end of cupola |
| of inner member | 256 edge |

Illustrative Examples of Device for Assembling Implant Systems

Turning now to the figures, FIG. 1 illustrates an example of a femoral head implant assembly system (device) 100, which may be referred to herein as an "assembly system" or simply as a "device" or "system" for ease of reference. The assembly system 100 has a proximal end 151 and a distal end 150. Components may be described herein with reference to having a distal end or a proximal end, and such references are in correspondence to the distal end 150 and the proximal end 151 of the assembly device 100, unless otherwise stated or illustrated or as discernable by the drawings or the context of the description.

The assembly system 100 includes a body 101 having a base portion ("base") 106 at the proximal end 151, a top portion 110 at the distal end 150, and a support 104 positioned between the base 106 and the top portion 110. In some embodiments, two or more of the base 106, the support 101, and/or the top portion 110 are integrally formed. In other embodiments, one or more of the base 106, the support 104, and/or the top portion 110 are separate pieces that are coupled together. In some embodiments, the base 106 includes a base support 108 on the portion of the base 106 near the head support 131. In some embodiments, the base support 108 is a half-circle and is attached at the front end of the base portion 106. In some embodiments the base support 108 is made of metal. In an example, the base support 108 can be curved or C-shaped. The support 104 can include a grip 105 which is sized and shaped to allow a user's hand to grasp the grip 105, at least partially encircling the grip 105 to stabilize the system 100 during operation and providing a safe place to hold (grip) the assembly system 100 set back from certain movable components (e.g., handle 102, rod 112, and stage 120) to protect the user's hand and fingers. For example, a user can stabilize the assembly system 100 by holding the grip 105 when moving the handle 102 from a first position A to a second position B while coupling the outer head and inner head. In this example, first position A is an upper position relative to second position B which is a lower position. When the handle 102 is moved from the first position A to the second position B, the assembly that couples the handle to a rod 112 correspondingly drives the rod 112 from a raised (distal) position to a lower (proximal) position to press an implant outer head onto an inner head, as illustrated in FIGS. 13A-13D. Movement of the handle from first position A to second position B correspondingly moves the rod 112 a certain distance towards the implant through use of a drive pawl 111, that engages with teeth on the rod 112 to move the rod. To continue to move the rod 112 towards the implant, the handle 102 may have to be moved back to the first position A, and then to the second position B in a ratchet-like manner (depending on the configuration of the assembly). A set pawl 230 in the assembly also engages with teeth on the rod 112 and holds the rod 112 in place during the ratchet-like process. Due to the pressure being applied on the implant, a significant amount of force can be on the set pawl 230 locking it tightly into the teeth. Embodiments of the set pawl 230 described herein prevent the rod 112 and set pawl 230 to become jammed together such that it is difficult to disengage the teeth 227 from the set pawl 230.

The top portion 110 includes an actuator system 132 with a locking assembly 128 (FIG. 3) for driving a rod 112 along a longitudinal axis 202 (FIG. 2) towards a head support 131, the head support 131 coupled to the base 106. Rod 112 has a proximal end 228 and a distal end 229. In this example, the rod 112 includes a knob 126 coupled to the distal end 229, which may be used to rotate the rod 112 around its longitudinal axis. In this example, a cupola 114 is coupled to the proximal end 228 of the rod 112. The cupola 114 includes a lower (proximal) surface 124 facing the base 106 that contacts an exterior surface of the outer head 134 when it presses an outer head 134 onto an inner head 133 (see FIGS. 13A-13D). In preferred embodiments, the surface 124 may be partly, or entirely, concave to provide a better fit of the surface 124 against the curved exterior surface (e.g., ball-like) of the outer head 134. The rod 112 includes a series of teeth 227 (FIG. 3) that are positioned along a surface 136 (FIG. 3) of rod 112, i.e., along a portion of the length of the rod 112. In this example, the teeth 227 are aligned perpendicular to a longitudinal axis 202 (FIG. 2) of the rod 112. The actuator system 132 also includes a drive pawl 111 (FIG. 3) and a set pawl 230 (see e.g., FIGS. 3 and 11A-11D) which are further described hereinbelow. The handle 102 is coupled to the drive pawl 111 such that when the handle is moved from a first position to a second position, the drive pawl 111 engages with the rod's teeth 227 and moves the rod 112 towards the base 106.

The locking assembly 128 includes a set pawl 230. While the drive pawl 111 drives the rod 112 downward to apply a force on a surface of the outer head, the set pawl 230 prevents the rod 112 from moving upwards (away from the base 106) while the handle 102 is moved to its first position. The set pawl 230 engages with the rod's teeth 227 each time the rod 112 is moved towards the base 106, in a ratchet-like manner. As described in more detail reference to FIGS. 11A-11D, the set pawl 230 includes a specially designed edge 256 that interfaces with the rod's teeth 227 to alleviate a binding condition that can occur when the user rotates the rod 112 to raise it off of the outer head.

The head support 131 provides support for both the inner head and the outer head while they are being coupled together. The head support 131 includes an inner member 122 which is coupled to the base 106. The inner member 122 includes a raised peripheral ridge 140, extending from above the surface 135, around the inner member 122 and adjacent to the bevel 141 which is on an outer surface of the ridge 140. The ridge 140 retains and aligns an inner head on the inner member 122. The head support 131 also includes an inner head support 116 extending from a distal surface (top surface) 135 of the inner member 122 towards the cupola 114. The inner head support 116 is shaped to fit inside a cavity in the inner head 133 to support and retain the inner head 133 in a certain position (upright) while the outer head 134 is pressed onto the inner head 133. The distal surface 135 of the inner member 122 is designed to support edges of the inner head 133 around its cavity. In some embodiments, the surface 135 includes indicia to help correctly place or center the outer head on the distal surface 135. In some examples, the distal surface 135 includes a ring 130. In some examples, the distal surface 135 includes one or more concentric rings 130 (see FIG. 8D).

The head support 131 further includes a stage 120. The stage 120 is structured to surround and move along the inner member 122 (e.g., vertically with respect to the orientation of FIG. 1). In other words, the stage 120 is slidably coupled to the inner member 122. In the illustrated embodiment the shape of an outer surface of the inner member 122 is cylindrical. In other embodiments, the shape of the outer surface of the inner member 122 may have other shapes (e.g., rectangular, multi-sided, hexagonal, curved, etc.).

In this example, the stage 120 includes a platform 103 at the distal end of the head support 131 facing the cupola 114. The platform 103 is arranged laterally around the inner member 122 and extends outward from the inner member 122. The platform 103 may be aligned substantially normal to an axis of the rod 112. The platform 103 has a surface 135. The stage 120 includes an aperture 109 (FIGS. 8C-8E) longitudinally oriented within the stage 120 and sized to fit around the inner member 122. A set of one or more structures (fingers) 121, as illustrated in FIGS. 8A, 8B, extend from a portion of the stage 120 in the aperture 109 and contact the inner member 122 such that the fingers 121 have a friction fit onto the inner member 122 allowing the stage 120 to be positioned at different heights on the inner member 122 and remain at there. In some embodiments, the structures 121 can be connected to a portion of the stage 120 at a distal end, and be unconnected at a proximal end such that although they are rigid or semi-rigid, they may move slightly to allow them to grip the inner member 122. That is, when the structures 121 are placed around the inner member 122 such that a portion of the inner member 122 is inside a portion of the stage 120, the structures 121 in contact with the inner member and are slightly flexed outward by the inner member 122. In an assembly operation, the stage 120 slides along the inner member 122 and around the inner femoral head and when the cupola 114 presses a large polyethylene liner 134, that rests on the stage 120, the stage 120 slides back to a proximal position (e.g., a lower position relative to the orientation of system 100 when in use). This way, the stage 120 provides a movable and stable support for the outer head 134 (e.g., a polyethylene liner) to rest on as it is pushed onto the inner head 133. This is further described in reference to FIGS. 13A-D.

Figure 2:
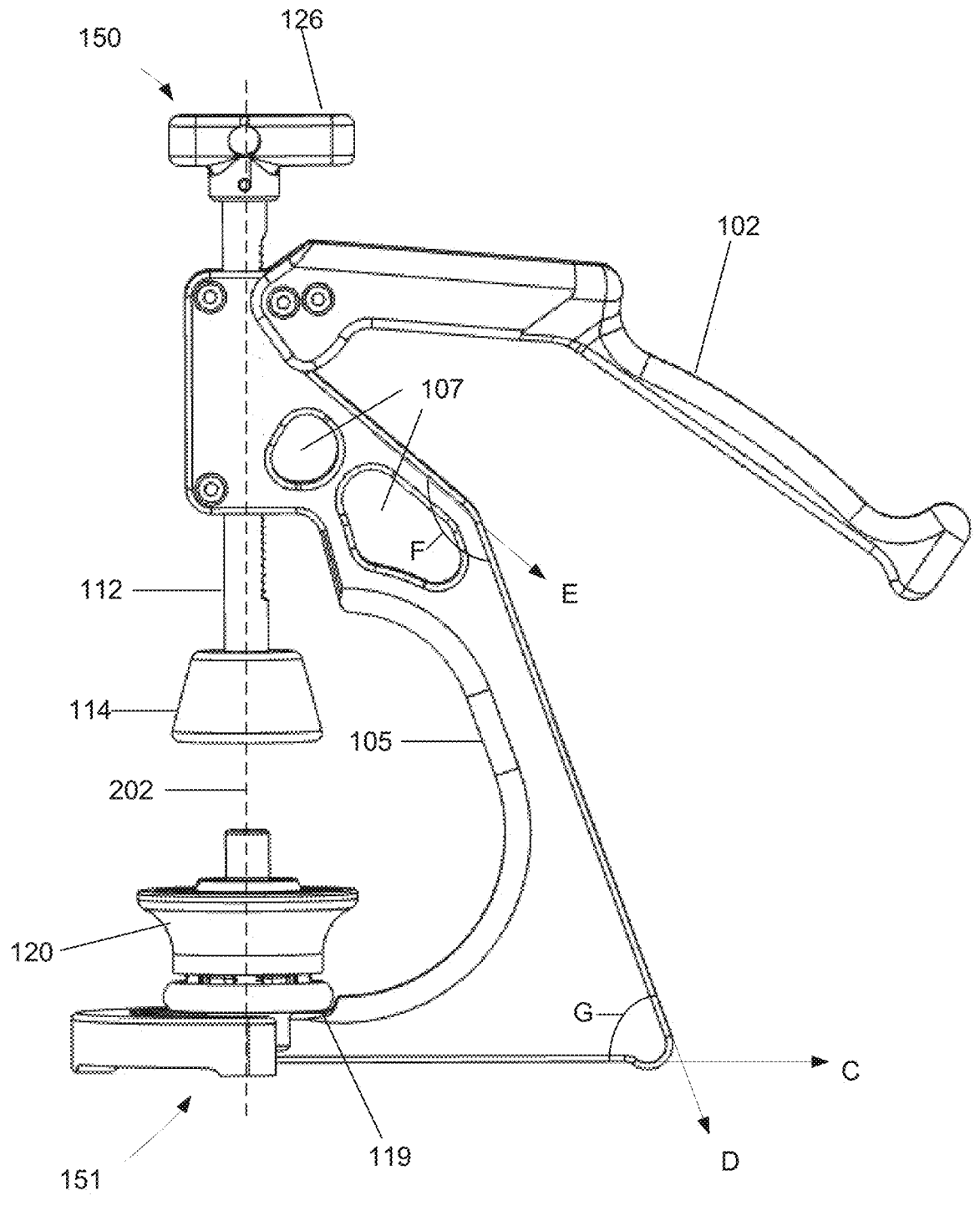
FIG. 2 illustrates the right-side view of the femoral head implant assembly device, in accordance with an illustrative embodiment.

FIG. 2 illustrates the right-side view of the femoral head implant assembly device 100 in FIG. 1 and the angles between such components. Various embodiments may be configured differently. In some embodiments, angle F between the top portion 110 and the body support member 104 is between about 148 degrees and about 153 degrees. In some embodiments, angle F between the top portion 110 and the body support member 104 is between about 90 degrees and about 180 degrees. In some embodiments, angle G between the body support member 104 and the base portion 106 is between about 68 degrees and about 72 degrees. In some embodiments, angle G between the body support member 104 and the base portion 106 is between about 45 degrees and about 90 degrees. In some embodiments, the grip 105 is made from plastic. In some embodiments, the grip 105 is made from a metal. In some embodiments the body has one or more cavities 107.

Figure 3:
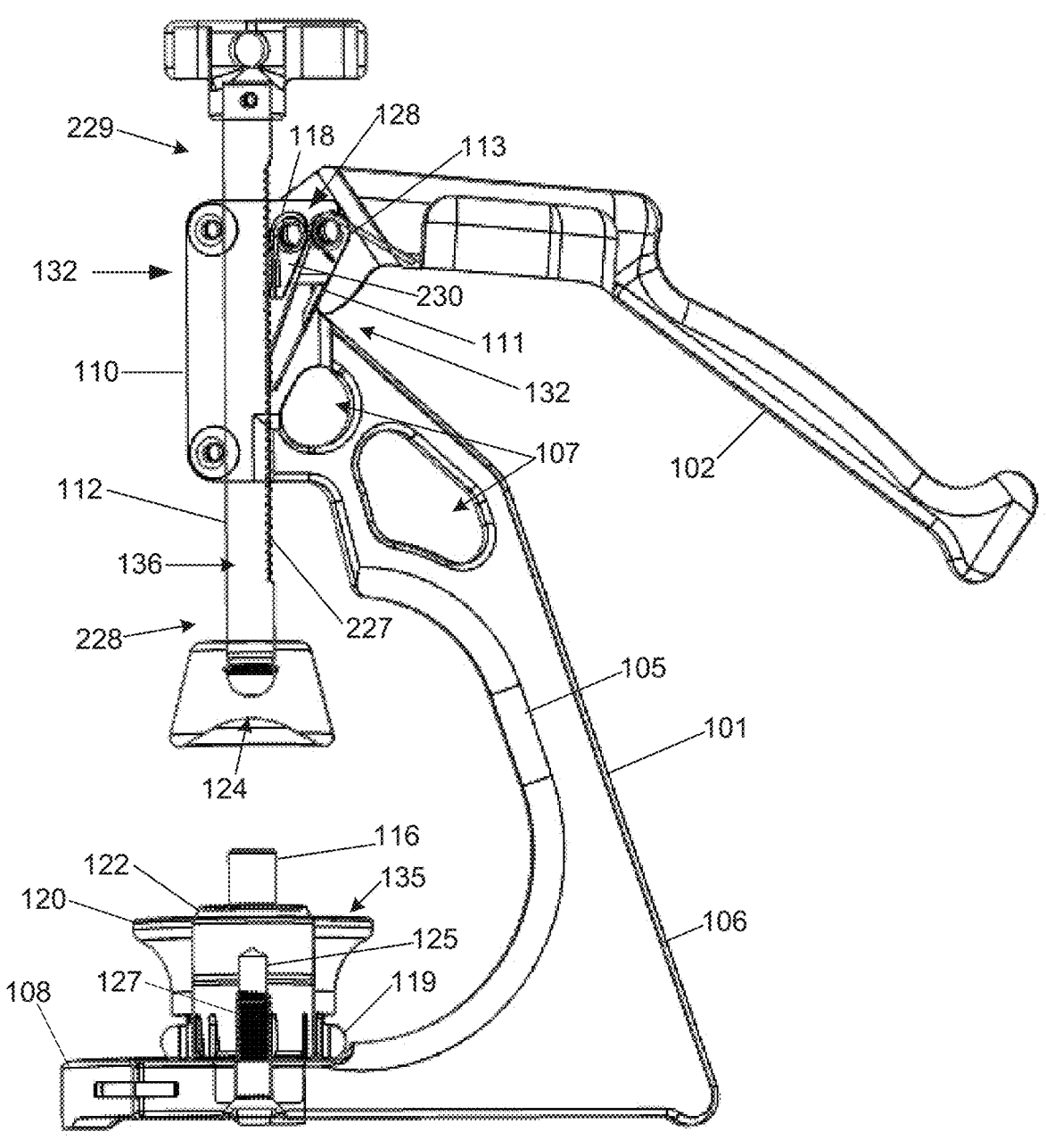
FIG. 3 illustrates a cross-sectional view of the femoral head implant assembly device, in accordance with an illustrative embodiment.

FIG. 3 illustrates further a cross-sectional view of the femoral head implant assembly device 100 from FIG. 1. In some embodiments, the cupola 114 has a distal end 252 and a proximal end 254 (see FIG. 10A). In some embodiments, the cupola 114 has a concave surface 124 on the proximal end 254 of the cupola 114.

Figure 4:
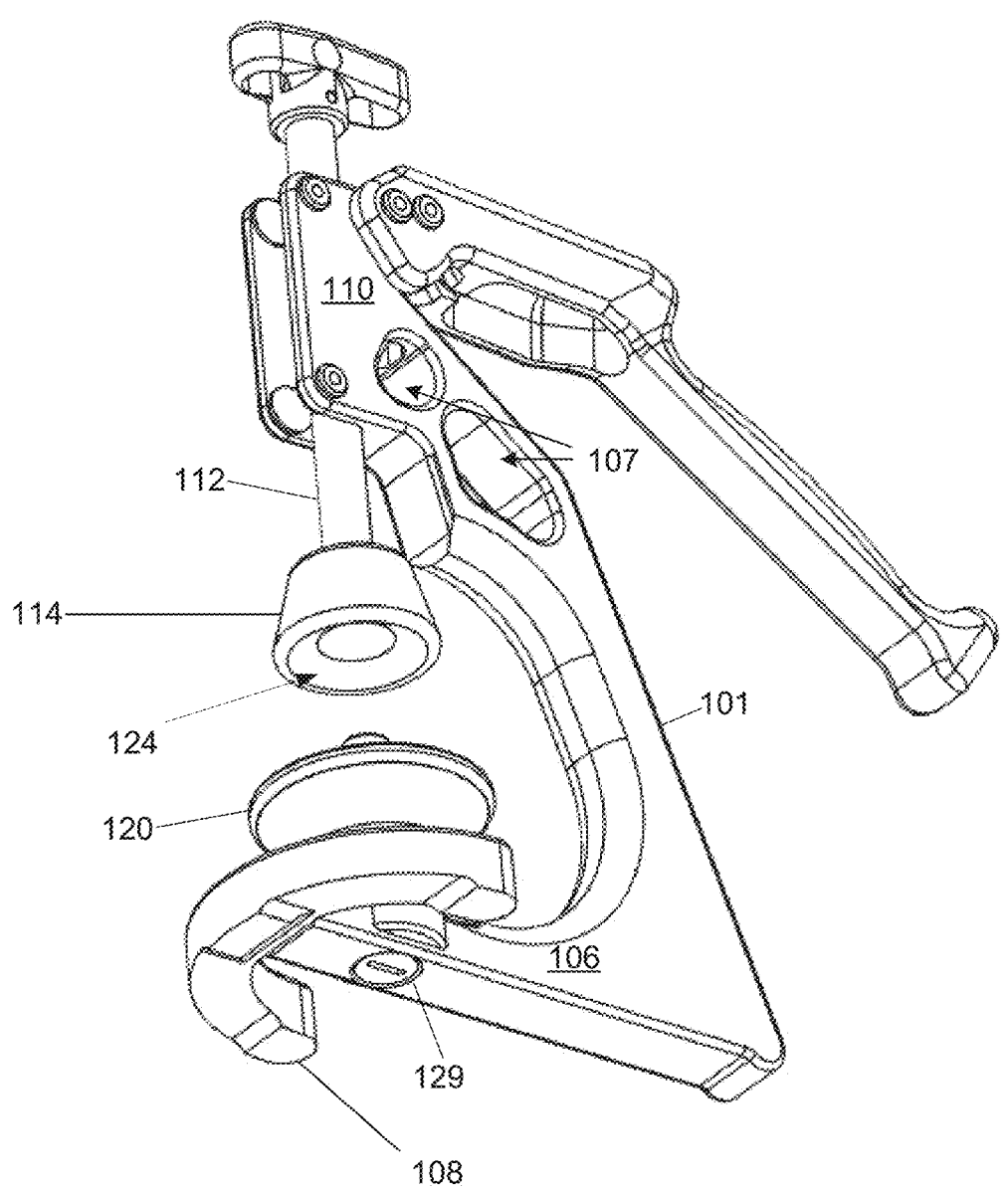
FIG. 4 illustrates a perspective view from the distal end of a femoral head implant assembly device in accordance with an illustrative embodiment.

FIG. 4 further illustrates a perspective view from the distal end of the femoral head implant assembly device 100 from FIG. 1.

Figure 5:
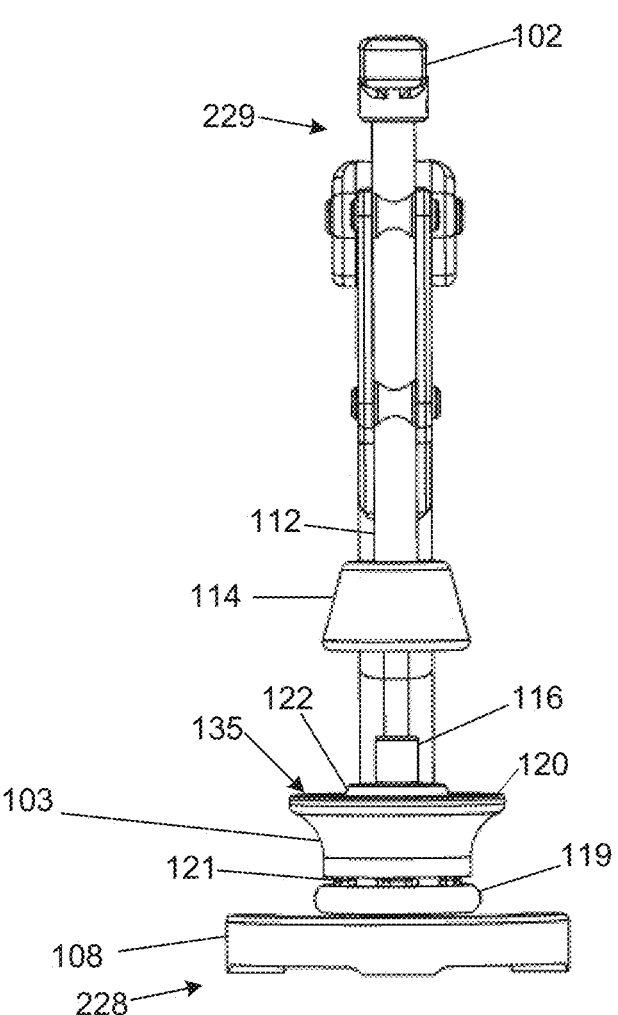
FIG. 5 illustrates a front view of a femoral head implant assembly device in accordance with an illustrative embodiment.

FIG. 5 further illustrates a front view of the femoral head implant assembly device 100 from FIG. 1.

Figure 6:
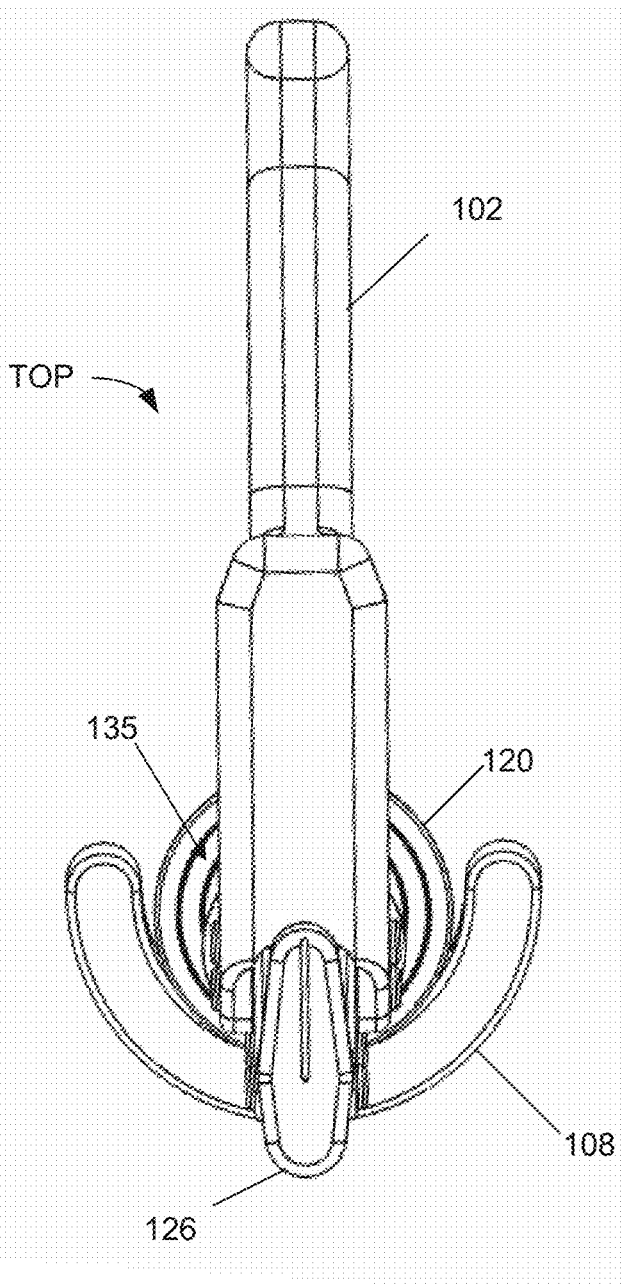
FIG. 6 illustrates a top view of a femoral head implant assembly device in accordance with an illustrative embodiment.

FIG. 6 further illustrates a top view of the femoral head implant assembly device 100 from FIG. 1.

Figure 7:
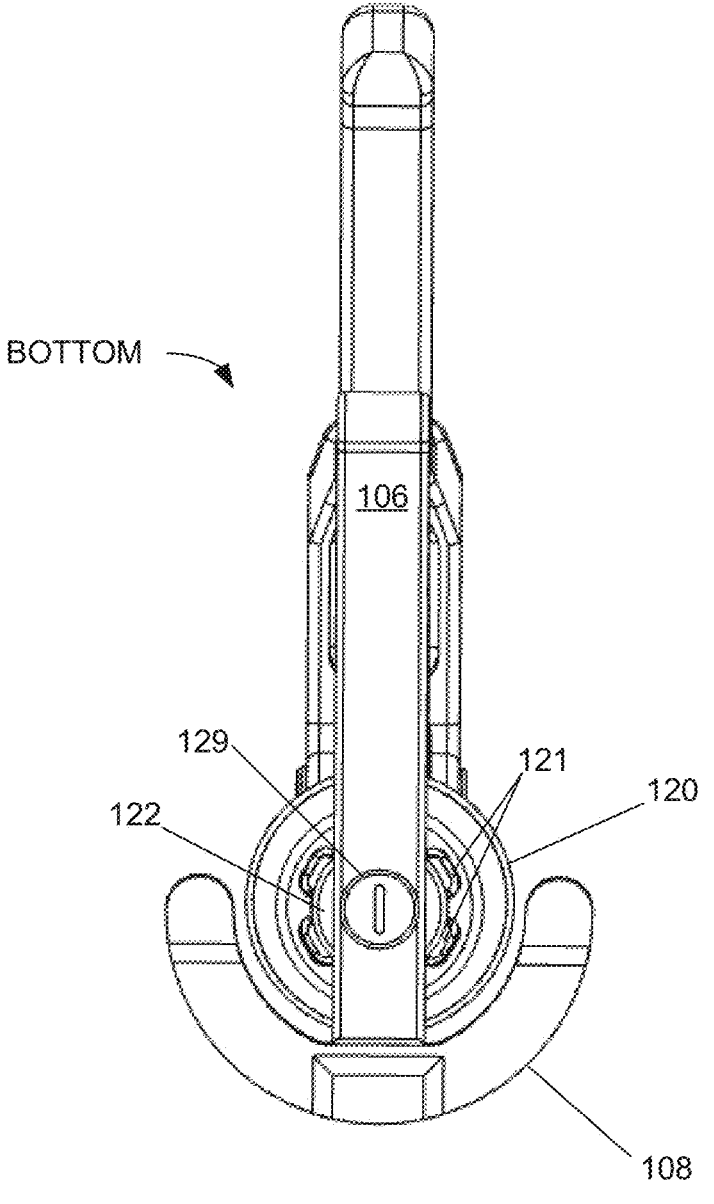
FIG. 7 illustrates a bottom view of a femoral head implant assembly device in accordance with an illustrative embodiment.

FIG. 7 further illustrates a bottom view of the assembly device 100 from FIG. 1.

FIGS. 8A-8E illustrate views of five sides of an example of the stage 120. The stage 120 has a proximal end 218 and a distal end 219. FIGS. 8A and 8B show perspective views of different angles from the distal end 219 of the stage 120. FIG. 8C is a perspective view of the side of the stage 120. FIG. 8D is a top view of the stage 120. FIG. 8E is a bottom view of the stage 120.

In some embodiments the stage 120 has at least one finger 121. In some embodiments the fingers 121 are used to create friction between the stage 120 and the inner member 122. In some embodiments, the stage 120 has a guard 119 that is positioned on the proximal end of the stage 120, the guard 119 extending laterally from the proximal end 218 of the stage 120 to at least partially shield the fingers 121 and the area where the stage 120 contacts the inner member 122 from contact by a user while providing a surface for the user to grip when actuating the stage 120 along the inner member 122. In some embodiments, the stage 120 has a flat distal surface 135, aligned substantially normal to the longitudinal axis 202. In some embodiments, the stage 120 has target rings 130a and 130b etched or marked on the distal surface 135. Target rings 130a, 130b are on the distal surface 135 and can be formed therein. The target rings 130a, 130b provide a reference for the user to properly center an outer head when it is placed on the stage 120. In some embodiments an exterior surface 220 at the distal end 219 of the stage 120 can be curved. In some embodiments the side surface 221 of the stage 120 is curved. In some embodiments, the radius of the top surface 135 is between about 15 and about 38 millimeters. In some embodiments, the radius of the top surface 135 is between about 25 and about 31 millimeters. In some embodiments, the radius of the top surface 135 is between about 26 millimeters and about 28 millimeters. In some embodiments, the first target ring 130a has a radius between about 18 mm to about 19 mm. In some embodiments, the first target ring 130a has a radius between about 15 mm to about 23 mm. The radius of the second target ring 130b is larger than the radius of the first target ring. In some embodiments the second target ring 130b has a radius between about 22 mm to about 23 mm. In some embodiments the second target ring 130b has a radius between about 20 mm to about 28 mm.

Figures 9A, 9B, 9C, 9D, 9E, 9F:
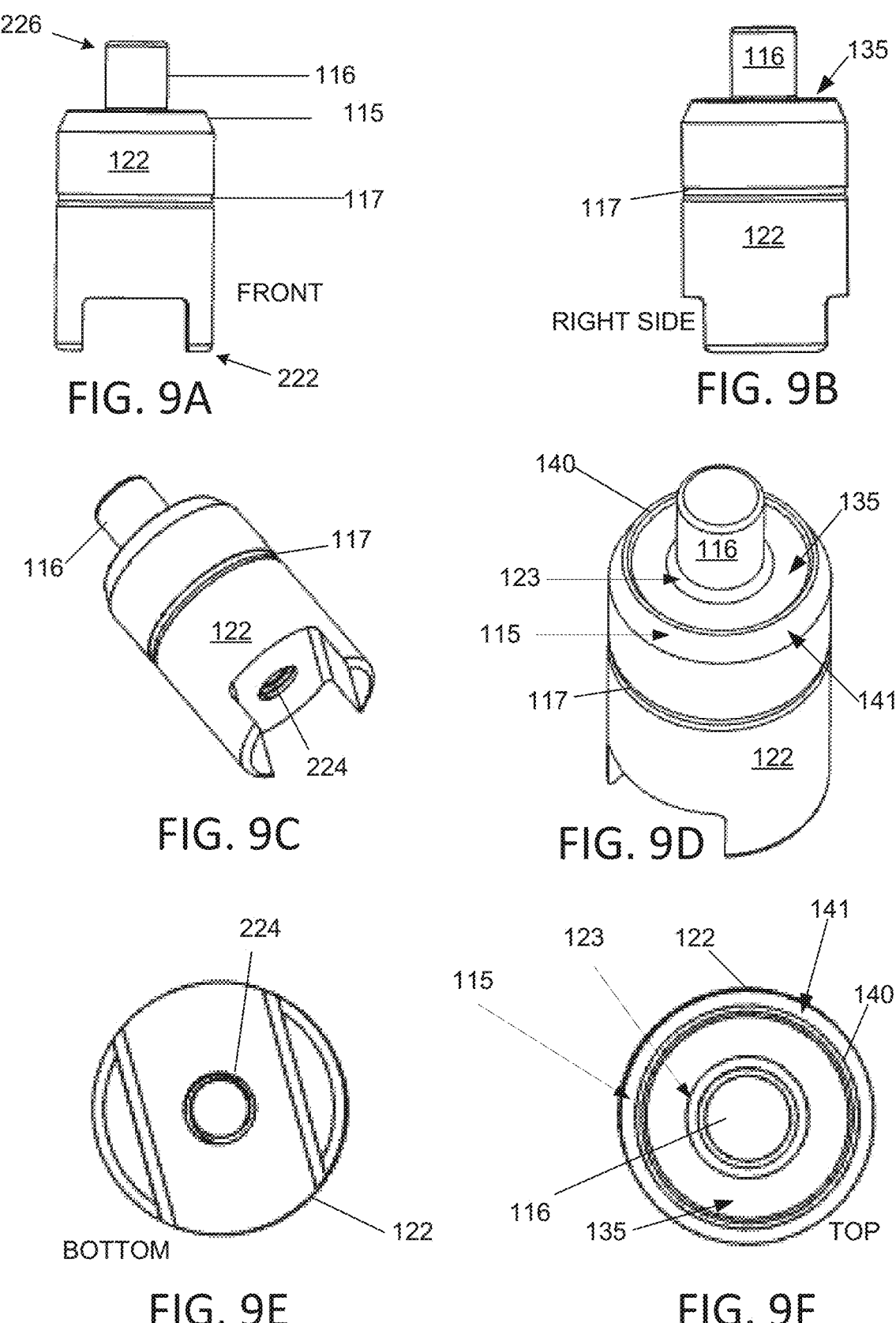
FIGS. 9A-9F illustrate views of six sides of an example of an inner member of a head support of a femoral head implant assembly system.

FIGS. 9A-9F illustrate views of six sides of an example of an inner member 122 of a head support 131 of a femoral head implant assembly system 100. FIG. 9A shows a front view of the inner member 122. FIG. 9B shows a side view of the inner member 122. FIG. 9C shows a perspective view of the proximal end 222 of the inner member 122. FIG. 9D shows a perspective view from the distal end 226 of the inner member 122. FIG. 9E shows a bottom view of the inner member 122. FIG. 9F shows a top view of the inner member 122.

Still referring to FIGS. 9A-9F, the inner member 122 has a proximal end 222 and a distal end 226. The inner head support 116 extends from the center of the top surface 135 of the inner member 122. In some embodiments, the inner head support 116 extends from the top surface 135 between about 10 mm to about 13 mm. In some embodiments, the inner head support 116 extends from the top surface 135 between about 5 mm and 20 mm. In some embodiments the inner head support 116 has a radius from about 3 mm to about 7 mm. In some embodiments the inner member 122 has a circumferential indent 117 on an exterior surface. In some embodiments, the inner member 122 includes an indent 117. The indent 117 can be aligned normal to the longitudinal axis of the inner member 122. In some embodiments the indent 117 is used as a stop for the fingers 121 to allow the stage 120 to be positioned at a certain height while it moves along the inner member 122 and further prevents the stage 120 from being pulled off the inner member 122. In some embodiments the inner member 122 has additional features to assist with the coupling of the inner member 122 to the stage 120.

In some embodiments, the distal end 226 of the inner member 122 has a beveled surface 141 along its curved edge 115. In some embodiments the beveled surface 141 allows for the inner head 133 and outer head 134 to assemble together completely. Once assembled, the outer head 134 may fully contain the inner head 133 (depending on the style of the inner head). During assembly, part or all of the inner member 122 may pass into a portion of the outer head 134 as the inner head 133 and outer head 134 are pressed together (for example, see FIGS. 13A-13D). In some embodiments, the inner member 122 is slanted on the proximal end 222. In some embodiments the inner head support 116 has a slanted, beveled, or curved edge 123 around the inner head support where it meets the inner member 122.

In an example, the depth of the circumferential indent 117 on the inner head support 116 is 0.010 inches. In another example, the depth of the circumferential indent 117 can be between about 0.008 inches and about 0.012 inches (e.g., 0.010 inches plus or minus 20%). In another example, the depth of the circumferential indent 117 can be between about 0.009 inches and about 0.011 inches (e.g., 0.010 inches plus or minus 10%).

Figure 10A:
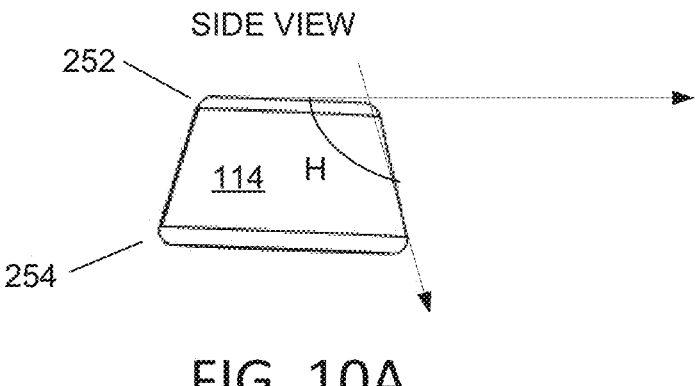
FIGS. 10A-10C illustrate a cupola shown in FIG. 1, in accordance with an illustrative embodiment, where
Figures 10B, 10C:
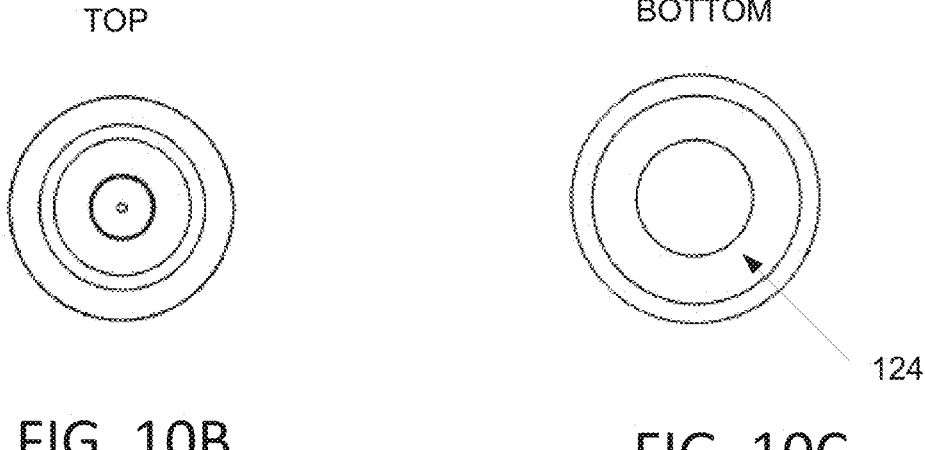

FIGS. 10A-10C illustrate views of three sides of an example of a cupola 114 of a femoral head implant assembly system 100. FIG. 10A shows a side view of the cupola 114. FIG. 10B shows a top view of the cupola 114. FIG. 10C shows a bottom view of the cupola 114. In some embodiments the cupola 114 has a proximal end 252 and a distal end 254. In some embodiments, at distal end 254 of the cupola surface is concave. In some embodiments the cupola 114 has a frustum shape.

FIGS. 11A-11D illustrate views of four sides of an example of a set pawl 230 of a femoral head implant assembly system 100. FIGS. 11A and 11B show perspective views of the set pawl 230 from different angles. FIG. 11C shows a left side view of the set pawl 230. FIG. 11D shows a right-side view of the set pawl 230. In some embodiments the set pawl has a proximal end 236 and a distal end 238. In some embodiments the set pawl is coupled to the top portion 110 of the femoral head implant assembly system 100 through holes 234 on either side of the set pawl. In the example illustrated, the holes 234 are elongated holes or non-symmetrical (e.g., oval-shaped). For example, as shown in FIG. 11C, the length 239 of the hole 234 is longer than the width 240 of the hole 234 such that the hole is not circular. In other embodiments, the holes 234 can be circular. Having elongated holes can help prevent jams that can occur when the cupola 114 is pressed tightly against an outer head. In this configuration, the elongated holes 234 provide strain relief and allow the rod 112 to be rotated to disengage the teeth 227 and the set pawl 230, allowing the set pawl 230 to move slightly longitudinally. In some embodiments the set pawl has a first portion 232 and a second portion 233 at the edge of the distal end of the set pawl 238. In some embodiments the first portion 232 is configured to engage the teeth of the rod 227. In some embodiments the second portion 233 of the set pawl 230 is of lesser stature than the first portion 232, so when the disengagement knob 126 is turned to move the rod 112, the set pawl 230 does not jam with the rod 112. In some embodiments, the set pawl 230 may include multiple edges 256 aligned in parallel and configured to engage with multiple teeth 227 of the rod. In such embodiments, each of the multiple edges may have a first portion 232 and a second portion 233, for example, as illustrated in FIG. 11A. In such embodiments, at least one of the multiple edges may have a first portion 232 and a second portion 233, for example, as illustrated in FIG. 11A.

Figures 12A, 12B, 12C, 12D:
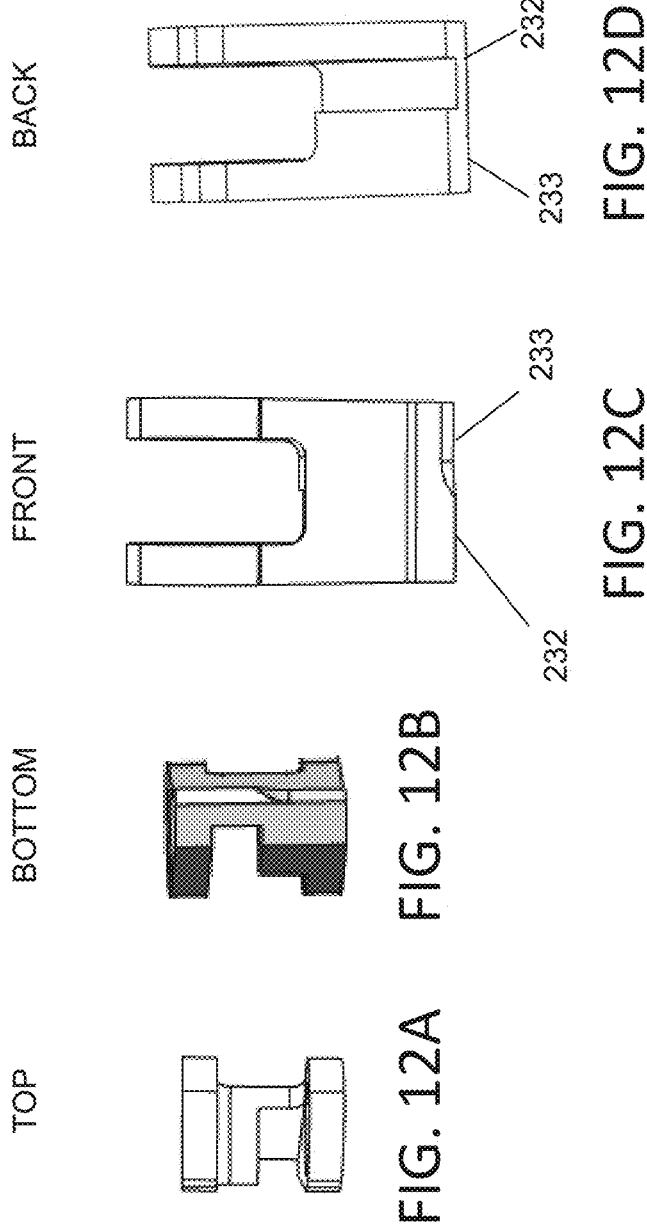
FIGS. 12A, 12B, 12C, and 12D depict the set pawl as shown in FIGS. 3, and 11, in accordance with an illustrative embodiment, where

FIGS. 12A-12D further illustrate views four sides of an example of a set pawl 230 of a femoral head implant assembly system 100. FIG. 12A illustrates a top view of a set pawl 230. FIG. 12B illustrates a bottom view of a set pawl 230. FIG. 12C illustrates a front view of a set pawl 230. FIG. 12D illustrates a back view of a set pawl 230.

Figures 13A, 13B, 13C, 13D:
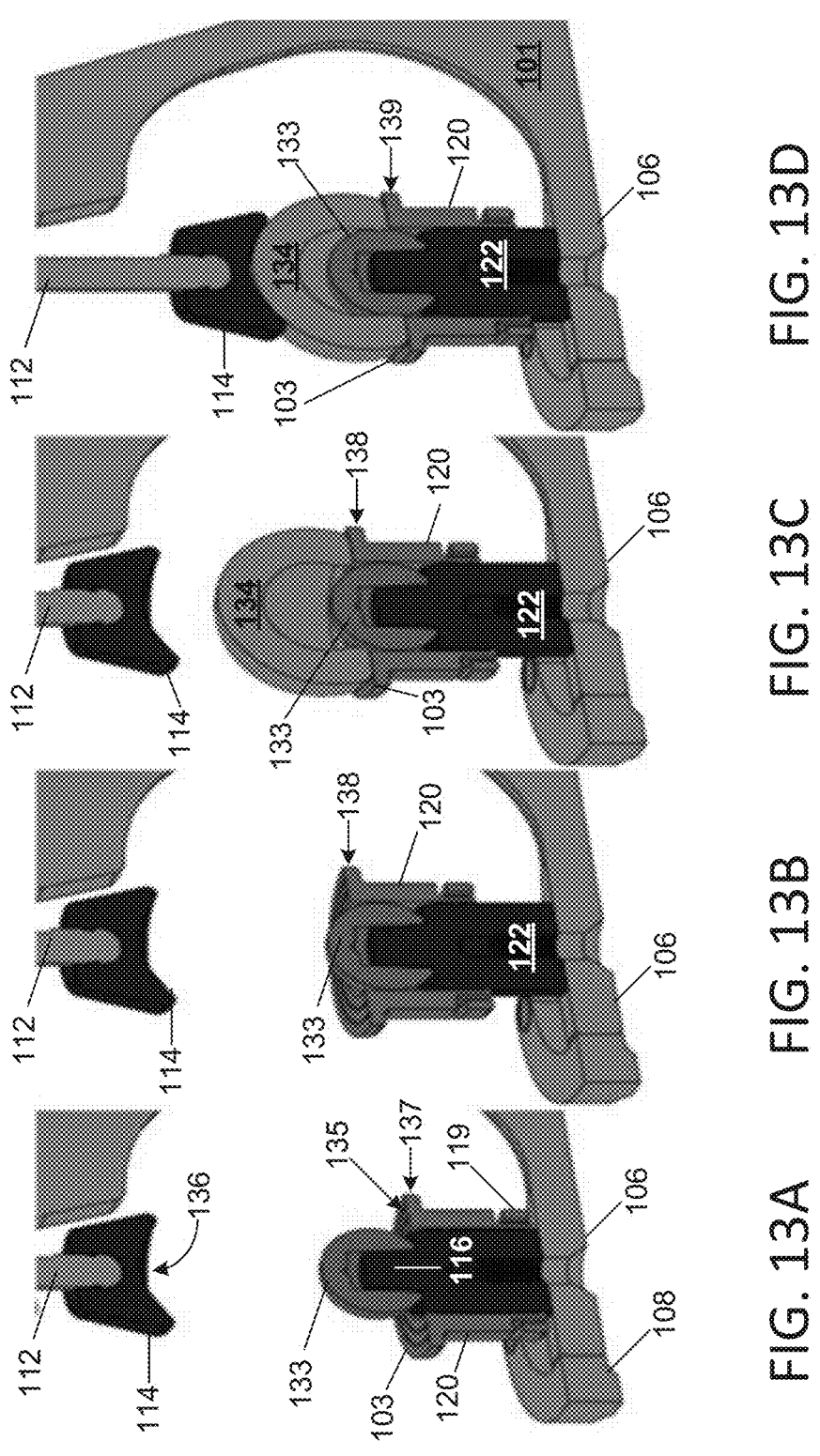
FIGS. 13A-13D illustrative an example of a "floating" or "movable" platform, according to some embodiments.

FIGS. 13A-13D illustrate the vertical positioning of the stage 120 relative to the inner member 122 during an assembly operation where the inner head 133 is positioned within the outer head 134. The stage 120 and the inner member 122 are configured such that the stage 120 can be positioned at various heights on the inner member 122. In FIG. 13A, the stage 120 and the cupola 114 are in a starting position. The stage 120 is positioned low on the inner member 122 such that the stage 120 is adjacent to the base 106. The inner head 133 is placed on the inner member 122 such that the inner head support 116 extends into the inner head 133. The platform 103 is at a first position 137. In FIG. 13B, the stage 120 has been moved up on the inner member 122 such that the platform 130 is at a second position 138 at or near the top of the inner head 133. FIG. 13B also illustrates how, in this position, the inner head 133 is in, or at least partially in, the aperture 109 of the stage 120. In FIG. 13C, the outer head 134 has been placed on the platform 103 above the inner head 133. Finally, in FIG. 13D the cupola 114 is driven downward and contacts an exterior surface of the outer head 134 to move the outer head 134 over the inner head 133 until the inner head 133 is within the outer head 134. As the cupola 114 applies force downward on the outer head 134, the outer head correspondingly applies a downward force on the stage 120 moving it towards the base 106 as the outer head 134 is pushed down over the inner head 133. Position 139 indicates a position of the platform 103 as the stage 120 is moved down the inner member 122. The fingers 121 (FIG. 8A) cause friction against the inner member 122 but allow the stage 120 to move, so that the platform 103 provides a movable support structure. Also, as the inner head 133 is at least partially within the aperture 109 of the stage 103, the interior wall of the aperture can provide lateral support (if necessary) to the inner head 133 to keep it vertically aligned such that it is positioned into the outer head 134 correctly. As the cupola 114 presses the outer head 134 downward, the inner head 133 is properly set into place with the outer head 134 and the assembly is complete.

In an example, the stage 120 can move 0.7 inches from the uppermost position to the lowest position. In another example, the stage 120 can move between about 0.56 inches and about 0.84 inches (e.g., 0.7 inches plus or minus 20%). In another example, the stage can move between about 0.63 inches and about 0.77 inches (e.g., 0.7 inches plus or minus 10%).

In some embodiments, the amount of force needed for the cupola 114 to press the outer head downward over the inner head 133 may be less for thinner large heads, for example about 2 kN of force. In other embodiments, more force may be needed with the large head is thicker, for example about 3.7 kN of force.

Figures 14A, 14B, 14C:
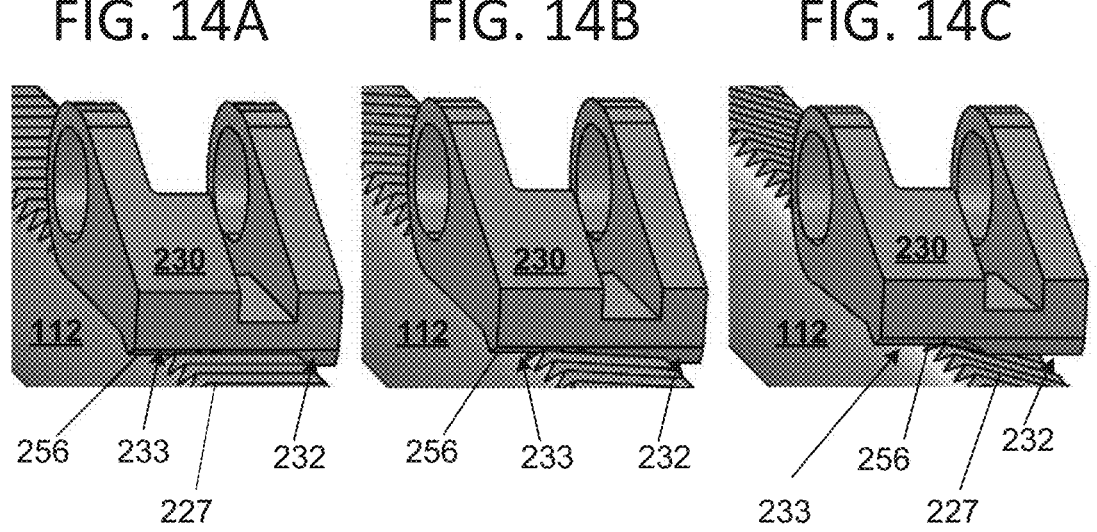
FIGS. 14A-14C further illustrate an example of a set pawl as it is engaged with the teeth on a rod, according to some embodiments.

FIGS. 14A-14C further illustrate the set pawl 230 as it is engaged with the set of teeth 227 on the rod 112. FIG. 14A illustrates that the set pawl 230 includes an edge 256 that engages the teeth 227 of the rod 112. FIG. 14A illustrates the first portion 232 engaged with the teeth 227 when the rod 112 is in a first position (e.g., the teeth oriented to be aligned with the edge 256). The second portion 233 is not engaged with the teeth 227 when the rod 112 is at a first position. The second portion 233 of the edge 256 has a setback region 235 (FIG. 11A) relative to the first portion 232. FIG. 14B illustrates the set pawl 230 positioned such that when the rod 112 is rotated (around its longitudinal axis) such that the teeth 227 are correspondingly rotated towards the first portion 232, and at least one of the teeth 227 extends into the setback region 235 (FIG. 11A) facilitating the disengagement of the teeth 227 with the set pawl 230. FIG. 14C illustrates the rod 112 being further rotated such that the teeth 227 are disengaging with the first portion 232 of the edge 256. The setback region 235 of the second portion 233 of the edge 256 allows the teeth 227 to more easily be disengaged from the set pawl 230 even when the rod 112 is under tension from having the cupola 114 forcibly pressed against the outer head 134 (e.g., as illustrated in FIG. 13D). Additionally, presence of the setback region 235 allows the pawl 230 to swing 'up' without jamming into the rod tooth with which it is engaged. Due to the setback region 235 being present only on one side of the pawl 230 'easy' disengaging of the pawl will only occur when the rod 112 is rotated counter-clockwise. Location of the pawl tooth relative to the space between the rod teeth and the underside of the pawl determine how the pawl is lifted.

In some embodiments, the set pawl 230 is made of metal or stainless steel, or some other corrosion resistant material.

In an example, the second portion 233 has a setback region distance 235 of 0.053 inches. In another example, the setback region distance 235 can be between about 0.0424 inches and about 0.0636 inches (e.g., 0.053 inches plus or minus 20%). In some embodiments, the setback region distance 235 has a length of any of or between any two of the following dimensions: 0.0424 inches, 0.045 inches, 0.0477 inches, 0.0503 inches, 0.053 inches, 0.0556 inches, 0.0583 inches, 0.0609 inches, and 0.0636 inches. In another example, the setback region distance 235 can be between about 0.0477 inches and about 0.0583 inches (e.g., 0.053 inches plus or minus 10%).

In an example, the teeth 227 are 0.031 inches off the rod 112. In another example, the teeth 227 can be between about 0.0248 inches and about 0.0372 inches (e.g., 0.031 inches plus or minus 20%). In another example, the teeth can be between about 0.0279 inches and about 0.0341 inches (e.g., 0.031 inches plus or minus 10%).

In an example, the width of the set pawl 230 is 0.425 inches. In another example, the width of the set pawl 230 can be between about 0.34 inches and about 0.51 inches (e.g., 0.425 inches plus or minus 20%). In another example, the width of the set pawl 230 can be between about 0.3825 inches and about 0.374 inches (e.g., 0.34 inches plus or minus 10%).

In an example, the second portion 233 is between about 33% and 53% of the setback region distance 235.

Figures 15A, 15B, 15C, 15D:
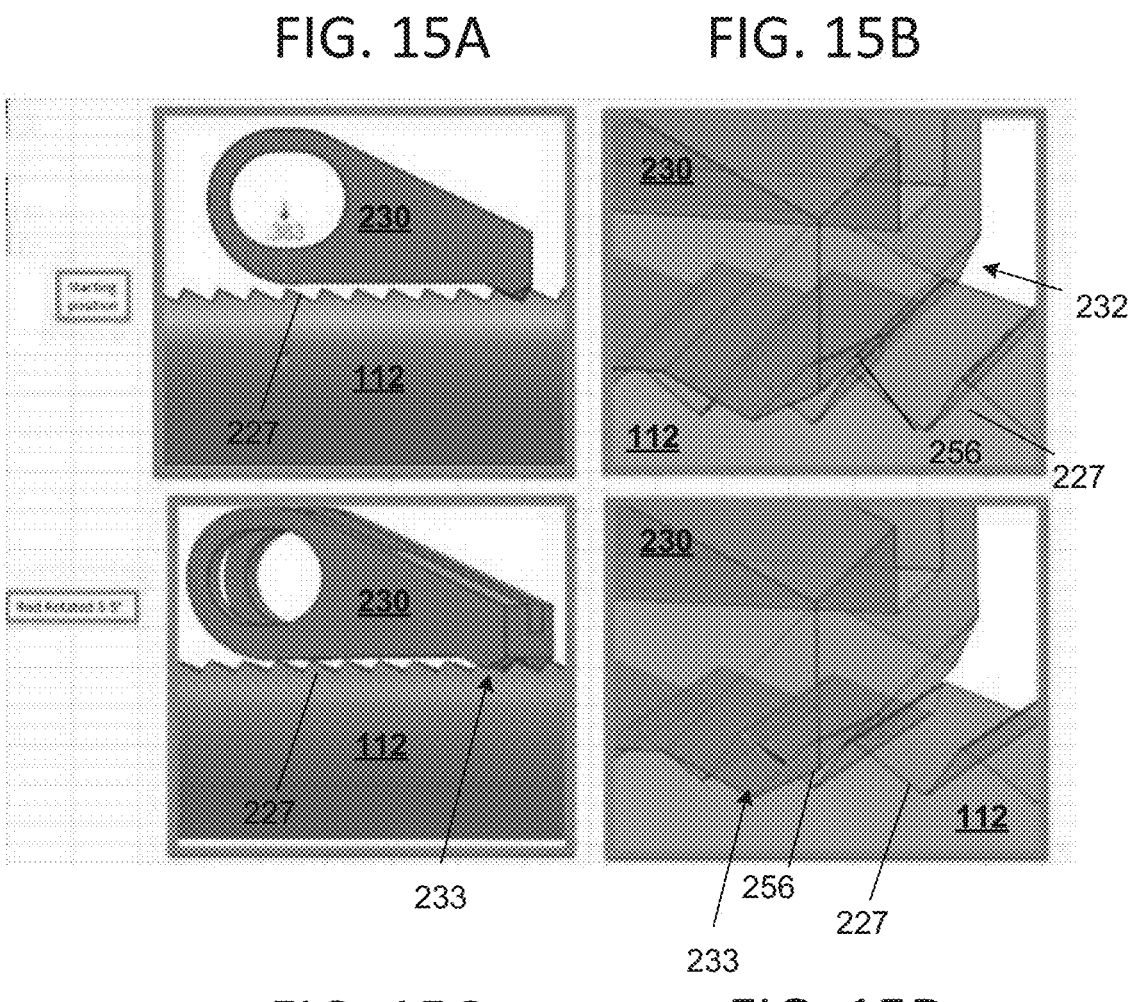
FIGS. 15A-15D illustrate another example of a set pawl as it is engaged with the teeth on a rod, according to some embodiments.

FIGS. 15A-15D further illustrate the set pawl 230 as it is engaged with the teeth 227 on the rod 112, according to some embodiments. In particular, these figures show the set pawl 230 in a starting position, then in a position after the rod 112 is turned and the teeth 227 begin to disengage. The first row, FIGS. 15A and 15B illustrate the set pawl 230 in a starting position where the surface 256 is engaged with the rod teeth 227. The second row, FIGS. 15C and 15D, illustrate the set pawl disengaged from the teeth 227 in a second position, and the area marked in red indicates the point of contact between the set pawl and the teeth. FIG. 15A is a side view of the starting position, and FIG. 15B is a close-up of the teeth 227 in contact with the set pawl 230. In some embodiments, the teeth 227 may begin to disengage when the rod is rotated 3 degrees, 4 degrees, or 5 degrees. As the rod teeth 227 rotate 'up' with the rotation of the rod 112, the set pawl 230 is lifted by the teeth making contact on the underside.

Figures 16A, 16B:
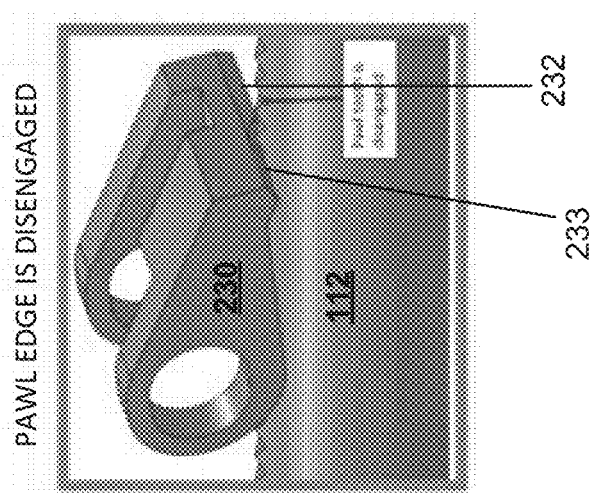
FIGS. 16A-16B illustrate the set pawl as it is disengages with the teeth on the rod, according to some embodiments.

FIGS. 16A and 16B illustrate the set pawl 230 as it is disengages with the teeth 227 on the rod 112, according to some embodiments. In some embodiments, the rod 112 is rotated 8 degrees, 9 degrees, or 10 degrees causing the teeth 227 of the set pawl 230 to disengage from the teeth of the rod 112. FIG. 16A is a side view of the disengaged set pawl 230 and FIG. 16B is a close up, ghost view of the set pawl 230 in contact with the teeth 227 of the rod 112.

Examples of an Assembly System Having the Disclosed Stage

Some (but not all) examples of embodiments of an assembly system, and/or components of an assembly system, for coupling together an inner head and an outer head of a femoral head implant are listed below, where the assembly system may include a movable stage, are listed below.

Embodiment 1: An assembly system, comprising: a handle; a rod coupled to the handle, the rod aligned along a longitudinal axis and coupled to the handle; a body comprising a distal end and a proximal end, the body having a base portion, a top portion, a support portion between the base portion and the top portion, the support portion including a grip for a user to hold while moving the handle, an actuator system coupled to the rod to move the rod along the longitudinal axis and to allow the rod to be at least partially rotated around the longitudinal axis; an implant support having an inner member coupled to the base portion and positioned between the rod and the base portion, the inner member extending from the base portion towards the top portion and aligned with the longitudinal axis; an inner head support extending from the distal end of the inner member towards the rod and configured to receive an inner head thereon, the inner head support aligned along the longitudinal axis with the rod, and a stage circumferentially positioned around and slidably coupled to the inner member such that the stage can move along an exterior surface of the inner member.

Embodiment 2: The assembly system of embodiment 1, further comprising a cupola having a distal end and a proximal end, the distal end of the cupola being coupled to the proximal end of the rod such that the cupola is positioned between the rod and the stage.

Embodiment 3: The assembly system of embodiment 2, wherein the cupola comprises a concave distal surface on a portion of the cupola surface that faces the stage for contacting a portion of an exterior surface of an outer head portion positioned on the platform.

Embodiment 4: The assembly system of embodiment 2, wherein the cupola is frustum shaped.

Embodiment 5: The assembly system of embodiment 1, wherein the stage has a proximal end and a distal end, and the stage comprises a platform on the distal end of the stage.

Embodiment 6: The assembly system of embodiment 5, wherein the platform is planar and aligned substantially normal to the longitudinal axis.

Embodiment 7: The assembly system of embodiment 5, wherein the stage comprises an aperture longitudinally positioned in the center of the platform sized such that the inner member sized to fit into the aperture.

Embodiment 8: The assembly system of embodiment 7, wherein the stage includes one or more structures positioned on the interior surface of the aperture and extending into the aperture, the one or more structures configured to provide contact the inner member and provide a friction between the inner member and the stage.

Embodiment 9: The assembly device of embodiment 7, wherein the stage includes a structure that contacts the inner member and provides friction between the stage and the inner member such that the stage can be moved along the inner member and be held in place at a position on the inner member by the friction between the stage and the inner member.

Embodiment 10: The assembly system of embodiment 8, wherein the one or more structures comprises a plurality of structures positioned symmetrically on the interior surface of the aperture.

Embodiment 11: The assembly system of embodiment 9, wherein the stage is movably positionable at different heights on the inner member.

Embodiment 12: The assembly system of embodiment 5, wherein the platform comprises indicia to guide placement of the outer head on the platform.

Embodiment 13: The assembly system of embodiment 12, wherein the indicia includes at least one ring surrounding the aperture Embodiment 14: The assembly system of embodiment 13, wherein the indicia includes two or more concentric rings.

Embodiment 15: The assembly system of embodiment 1, wherein the stage comprises a guard positioned circumferentially around the proximal end of the stage.

Embodiment 16: The assembly system of embodiment 1, further comprising a base support coupled to the base and extends laterally on either side of the base portion.

Embodiment 17: The assembly system of embodiment 16, wherein the base support is U-shaped and is coupled to the base portion at the center of the inside of the U-shape such that the base support extends laterally around part of the base portion.

Embodiment 18: The assembly system of embodiment 1, wherein the body comprises one or more cavities for reducing weight of the assembly device.

Embodiment 19: The assembly system of embodiment 1, wherein the rod comprises a knob coupled to the distal end of the rod for rotating the rod around the longitudinal axis.

Embodiment 20: An assembly system for coupling together an inner head and an outer head of a femoral head implant, the assembly device comprising: a body having a top portion and a base portion; a rod having a distal end and a proximal end, the rod coupled to the top portion and aligned along a longitudinal axis; a head support having an inner member coupled to a base portion, the head support positioned between the proximal end of rod and the base portion, the head support having an inner head support extending from the inner member towards the proximal end of the rod and configured to receive an implant inner head thereon, the inner head support aligned along the longitudinal axis, and a stage circumferentially positioned around, and slidably coupled to, the inner member such that the stage can move along an exterior surface of the inner member, the stage being aligned substantially normal to the longitudinal axis and configured to receive an outer implant head thereon. Examples of an Assembly System having the Disclosed Set Pawl Some, but not all, examples of embodiments of an assembly system, and/or components of an assembly system, for coupling together an inner head and an outer head of a femoral head implant are listed below, where the assembly system may include set pawl, are listed below.

Embodiment 1: A femoral head implant assembly system for coupling together an inner head and an outer head portion, the assembly device comprising a set pawl configured to engage teeth on a rod and hold the rod in place while a handle that is coupled to the rod is moved from a second position to a first position, the first position being a position where the handle can be moved to move the rod to push an outer head portion of an implant onto an inner head portion of the implant, the set pawl having an edge that includes a first portion and a second portion, the second portion having a setback region such that the first portion of the edge extends farther than the second portion of the edge.

Embodiment 2: The femoral head implant assembly system of claim 1, wherein the distance of the second portion setback region is 0.053" plus or minus 20%.

Embodiment 3: The femoral head implant assembly system of claim 1, wherein the distance of the second portion setback region is 0.053" plus or minus 10%.

Embodiment 4: The femoral head implant assembly system of claim 1, wherein the distance of the second portion setback region is 0.053" plus or minus 5%.

Embodiment 5: The femoral head implant assembly system of claim 1, wherein the length of the second portion is between about 33% and 53% of the length of the first portion.

Embodiment 6: The femoral head implant assembly system of claim 1, wherein the length of the second portion is between about 0.140 inches and 0.225 inches, and the edge of the set pawl is about 0.425 inches in length, plus or minus 20%.

Embodiment 7: The femoral head implant assembly system of claim 1, further comprising: a body comprising a distal end and a proximal end, the body having a base portion, a top portion, and a support portion between the base portion and the top portion, the support portion including a grip for a user to hold while moving the handle; an actuator system coupled to the rod to move the rod along the longitudinal axis and to allow the rod to be at least partially rotated around the longitudinal axis, the actuator system comprising a drive pawl coupled to the handle and configured to engage the rod and drive the rod along the longitudinal axis towards the base portion when the handle is moved from a first position to a second position, and the set pawl; and a support platform for holding an implant, the support platform aligned with the longitudinal axis in a position such that a proximal end of the rod moves towards the support platform when the handle is actuated.

Embodiment 8: The assembly device of claim 7, further comprising a cupola coupled to the proximal end of the rod such that the cupola is positioned between the rod and the stage.

Embodiment 9: The assembly device of claim 8, wherein the cupola comprises a concave surface on a portion of the cupola surface that faces the stage to contact a portion of an exterior surface of an outer head portion positioned on the platform.

Embodiment 10: The assembly device of claim 8, wherein the cupola is frustum shaped.

Embodiment 11: The assembly device of claim 7, wherein the set pawl includes a distal end and a proximal end, wherein the distal end is movably coupled to the actuator system.

Embodiment 12: The assembly device of claim 7, wherein the set pawl further comprises elongated holes that are used to couple the set pawl to the body Embodiment 13: The assembly device of claim 1, wherein the first portion of the edge has a curved transition to the second portion of the edge.

Embodiment 14: The assembly device of claim 1, wherein the rod comprises teeth on a surface of the rod extending along at least part of the length of the rod, wherein the first portion of the edge of the set pawl is positioned to engage with teeth on the surface of the rod when the teeth are positioned adjacent to the first portion.

Embodiment 15: The assembly device of claim 14, wherein the teeth are aligned perpendicular to the length of the rod.

Embodiment 16: The assembly device of claim 15, wherein the set pawl is positioned such that the first portion engages with the teeth of the rod and the second portion does not engage with teeth of the rod when the rod is positioned with the teeth of the rod aligned in parallel with the edge of the set pawl.

Embodiment 17: The assembly device of claim 15, wherein the set pawl is positioned such that when the rod is rotated, the teeth are rotated towards the first portion, a least one of the teeth extends into the setback region facilitating disengagement of the teeth with the set pawl.

Embodiment 18: An assembly device comprising a set pawl having an edge that includes a first portion and a second portion, the second portion having a setback region such that the first portion of the edge extends a distance of about 0.042 inches and about 0.064 inches farther than the second portion of the edge.

Embodiment 19: The assembly device of claim 18, wherein the set pawl is positioned to engage teeth on a rod and hold the rod in place while a handle that is coupled to the rod is moved from a second position to a first position, wherein moving the handle from the first position to the second position moves the rod to push an outer head portion of an implant onto an inner head portion of the implant.

Embodiment 20: A femoral head implant assembly system for coupling together an inner head and an outer head portion, the assembly device comprising a set pawl having an edge that includes a first portion and a second portion, the second portion having a setback region such that the first portion of the edge extends farther than the second portion of the edge, and the first portion has a curved transition to the second portion.

In some embodiments, an assembly system includes the disclosed movable stage and the disclosed set pawl. For example, the assembly system in FIG. 1 (and other figures) includes a movable stage and a set pawl, as described in the corresponding description.

Implementation Considerations

The foregoing description details certain embodiments of the systems, devices, and methods disclosed herein. It will be appreciated, however, that no matter how detailed the foregoing appears in text, the systems, devices, and methods can be practiced in many ways. As is also stated above, it should be noted that the use of particular terminology when describing certain features or aspects should not be taken to imply that the terminology is being re-defined herein to be restricted to including any specific characteristics of the features or aspects of the technology with which that terminology is associated.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Headings are included herein for reference and to aid in locating various sections. These headings are not intended to limit the scope of the concepts described with respect thereto. Such concepts may have applicability throughout the entire specification.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

The phrase "based on" does not mean "based only on," unless expressly specified otherwise. In other words, the phrase "based on" describes both "based only on" and "based at least on." Unless otherwise explicitly stated, articles such as "a" or "an" should generally be interpreted to include one or more described items. Accordingly, phrases such as "a device configured to" are intended to include one or more recited devices.

It will be appreciated by those skilled in the art that various modifications and changes may be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the figures may be combined, interchanged or excluded from other embodiments.

The above description discloses several methods and systems of certain embodiments. These embodiments are susceptible to modifications. Such modifications will become apparent to those skilled in the art from a consideration of this disclosure or practice of the embodiments disclosed herein. Consequently, it is not intended that this invention be limited to the specific embodiments disclosed herein, but that it cover all modifications and alternatives coming within the true scope and spirit of the invention as embodied in the attached claims.

Applicant reserves the right to submit claims directed to combinations and sub-combinations of the disclosed inventions that are believed to be novel and non-obvious. Inventions embodied in other combinations and sub-combinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the embodiments of the inventions described herein.

What is claimed is:

1. An implant assembly system for coupling together an inner implant and an outer implant portion of an implant, the assembly system comprising:

a set pawl configured to engage teeth on a rod and hold the rod in place while a handle that is coupled to the rod is moved from a second position to a first position, wherein the first position is a position where the handle can be moved to move the rod to push the outer implant portion of the implant onto the inner implant portion of the implant, wherein the set pawl includes an edge that includes a first portion and a second portion, the second portion having a setback region such that the first portion of the edge extends farther than the second portion of the edge, and wherein a width of the set pawl along the edge is greater than a width of the first portion along the edge.

2. The implant assembly system of claim 1, wherein the distance of the second portion setback region is 0.053" plus or minus 20%.

3. The implant assembly system of claim 1, wherein the distance of the second portion setback region is 0.053" plus or minus 10%.

4. The implant assembly system of claim 1, wherein the distance of the second portion setback region is 0.053" plus or minus 5%.

5. The implant assembly system of claim 1, wherein the length of the second portion is between about 33% and 53% of the length of the first portion.

6. The implant assembly system of claim 1, wherein the length of the second portion is between about 0.140 inches and 0.225 inches, and the edge of the set pawl is about 0.425 inches in length, plus or minus 20%.

7. The implant assembly system of claim 1, further comprising:

a body comprising a distal end and a proximal end, the body having a base portion, a top portion, and a support portion between the base portion and the top portion, the support portion including a grip for a user to hold while moving the handle;

an actuator system coupled to the rod to move the rod along the longitudinal axis and to allow the rod to be at least partially rotated around the longitudinal axis, the actuator system comprising a drive pawl coupled to the handle and configured to engage the rod and drive the rod along the longitudinal axis towards the base portion when the handle is moved from a first position to a second position, and the set pawl; and a support platform for holding an implant, the support platform aligned with the longitudinal axis in a position such that a proximal end of the rod moves towards the support platform when the handle is actuated.

8. The implant assembly system of claim 7, further comprising a cupola coupled to the proximal end of the rod such that the cupola is positioned between the rod and the support platform.

9. The implant assembly system of claim 8, wherein the cupola comprises a concave surface on a portion of the cupola surface that faces the support platform to contact a portion of an exterior surface of the outer implant portion positioned on the platform.

10. The implant assembly system of claim 8, wherein the cupola is frustum shaped.

11. The implant assembly system of claim 7, wherein the set pawl includes a distal end and a proximal end, wherein the distal end is movably coupled to the actuator system.

12. The implant assembly system of claim 7, wherein the set pawl further comprises elongated holes that are used to couple the set pawl to the body.

13. The implant assembly system of claim 1, wherein the first portion of the edge has a curved transition to the second portion of the edge.

14. The implant assembly system of claim 1, wherein the rod comprises the teeth on a surface of the rod extending along at least part of the length of the rod, wherein the first portion of the edge of the set pawl is positioned to engage with teeth on the surface of the rod when the teeth are positioned adjacent to the first portion.

15. The implant assembly system of claim 14, wherein the teeth are aligned perpendicular to the length of the rod.

16. The implant assembly system of claim 15, wherein the set pawl is positioned such that the first portion engages with the teeth of the rod and the second portion does not engage with teeth of the rod when the rod is positioned with the teeth of the rod aligned in parallel with the edge of the set pawl.

17. The implant assembly system of claim 15, wherein the set pawl is positioned such that when the rod is rotated, the teeth are rotated towards the first portion, a least one of the teeth extends into the setback region facilitating disengagement of the teeth with the set pawl.

18. An implant assembly device comprising:

a set pawl configured to engage teeth on a rod and including an edge that includes a first portion and a second portion, wherein the second portion includes a setback region such that the first portion of the edge extends a distance of about 0.042 inches and about 0.064 inches farther than the second portion of the edge, the second portion having a setback region such that the first portion of the edge extends farther than the second portion of the edge, and wherein a width of the set pawl along the edge is greater than a width of the first portion along the edge.

19. The implant assembly device of claim 18, wherein the set pawl is positioned to hold the rod in place while a handle that is coupled to the rod is moved from a second position to a first position, wherein moving the handle from the first position to the second position moves the rod to push an outer implant portion of an implant onto an inner implant portion of the implant.

20. An implant assembly system for coupling together an inner implant and an outer implant portion, the assembly system comprising:

a set pawl configured to engage teeth on a rod and including an edge that includes a first portion and a second portion, wherein the second portion includes a setback region such that the first portion of the edge extends farther than the second portion of the edge, wherein the first portion has a curved transition to the second portion, and wherein a width of the set pawl along the edge is greater than a width of the first portion along the edge.

* * * * *